United States Patent
Iwaki

(10) Patent No.: US 11,871,903 B2
(45) Date of Patent: Jan. 16, 2024

(54) ENDOSCOPIC IMAGE PROCESSING APPARATUS, ENDOSCOPIC IMAGE PROCESSING METHOD, AND NON-TRANSITORY COMPUTER READABLE RECORDING MEDIUM

(71) Applicant: OLYMPUS CORPORATION, Tokyo (JP)

(72) Inventor: Hidekazu Iwaki, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 494 days.

(21) Appl. No.: 17/126,537

(22) Filed: Dec. 18, 2020

(65) Prior Publication Data

US 2021/0106208 A1   Apr. 15, 2021

Related U.S. Application Data

(63) Continuation of application No. PCT/JP2018/023341, filed on Jun. 19, 2018.

(51) Int. Cl.
*A61B 1/00*   (2006.01)

(52) U.S. Cl.
CPC .... *A61B 1/000094* (2022.02); *A61B 1/00013* (2013.01); *A61B 1/00045* (2013.01); *A61B 1/000095* (2022.02)

(58) Field of Classification Search
CPC .......... A61B 1/000095; A61B 1/00045; A61B 1/00013; A61B 1/000094; A61B 1/0005;
(Continued)

(56) References Cited

U.S. PATENT DOCUMENTS 9,392,942 B2 * 7/2016 Shida ................ A61B 1/0005
2011/0254937 A1 * 10/2011 Yoshino ............. A61B 1/0655
348/E7.085
(Continued)

FOREIGN PATENT DOCUMENTS

EP    2926713 A1   10/2015
JP    201110841 A    1/2011
(Continued)

OTHER PUBLICATIONS

International Search Report dated Sep. 11, 2018 issued in PCT/JP2018/023341, 4 pages.

*Primary Examiner* — Timothy J Neal
(74) *Attorney, Agent, or Firm* — Scully, Scott, Murphy & Presser, P.C.

(57) ABSTRACT

An endoscopic image processing apparatus includes an image acquiring unit, a region-of-interest detection unit, a detection cessation determination unit, a display determination unit, and a display output unit. The detection cessation determination unit determines whether a detection of a region of interest in the region-of-interest detection unit has ceased. The display determination unit performs a display propriety determination as a determination of whether to display assisting information on a display unit, when a cessation determination is acquired in the detection cessation determination unit. The assisting information is information for assisting the region of interest, the detection of which has ceased, to be restored on a screen of a display unit.

18 Claims, 13 Drawing Sheets

(58) Field of Classification Search
CPC ....... A61B 1/0655; A61B 1/0669; A61B 1/05; A61B 1/00006; A61B 1/043; A61B 1/0646; A61B 1/00055; A61B 1/0638; H04N 7/183; G16H 40/63
See application file for complete search history.

(56) References Cited

U.S. PATENT DOCUMENTS

| | | | |
|---|---|---|---|
| 2012/0330165 A1* | 12/2012 | Watanabe | A61B 1/043 600/476 |
| 2014/0049626 A1* | 2/2014 | Ishihara | G01N 21/64 348/68 |
| 2015/0257635 A1 | 9/2015 | Kubo et al. | |
| 2020/0037856 A1* | 2/2020 | Watanabe | A61B 1/00045 |
| 2021/0022586 A1* | 1/2021 | Mori | A61B 1/00006 |

FOREIGN PATENT DOCUMENTS

| | | | |
|---|---|---|---|
| JP | 2011224038 A | 11/2011 | |
| JP | 2011255006 A | 12/2011 | |
| JP | 2013231772 A | 11/2013 | |
| JP | 5597021 B2 | 10/2014 | |
| JP | 2019-180966 A | 10/2019 | |
| WO | 2014084134 A1 | 6/2014 | |
| WO | 2018078724 A1 | 5/2018 | |
| WO | 2019106712 A1 | 6/2019 | |

* cited by examiner

ENDOSCOPIC IMAGE PROCESSING APPARATUS, ENDOSCOPIC IMAGE PROCESSING METHOD, AND NON-TRANSITORY COMPUTER READABLE RECORDING MEDIUM

CROSS-REFERENCE TO RELATED APPLICATION

This application is a continuation application of PCT/JP2018/023341 filed on Jun. 19, 2018, the entire contents of which are incorporated herein by this reference.

BACKGROUND OF THE INVENTION

1. Field of the Invention

The present invention relates to an endoscopic image processing apparatus, an endoscopic image processing method, and a non-transitory computer readable recording medium.

2. Description of the Related Art

Conventionally, in endoscope apparatuses, an operator has determined a presence or absence of a lesion part by viewing an observation image. Techniques for displaying information for assisting an endoscopic examination (hereinafter, referred to as assisting information) have been proposed, in order to prevent an operator from overlooking a lesion part when viewing an observation image. Japanese Patent Application Laid-Open Publication No. 2011-255006, for example, discloses an endoscope apparatus configured to display an observation image by adding an alert image to a detected region of interest by image processing.

In addition, Japanese Patent No. 5597021, for example, discloses an image processing apparatus for an endoscope system. The image processing apparatus is configured to detect a region of interest based on feature values calculated in a plurality of local regions in an image, estimate a position of the region of interest disappeared from a display target range by using information on the detected region of interest, which was obtained before the region of interest disappeared from the display target range, and display disappearance direction information as guiding information to the disappeared region of interest.

SUMMARY OF THE INVENTION

An endoscopic image processing apparatus according to one aspect of the present invention is an endoscopic image processing apparatus including a processor, and the processor is configured to: acquire an image of an object photographed by an endoscope; output an image for display including at least the acquired image to a monitor apparatus; detect a region of interest included in the acquired image; determine whether a detection of the region of interest has ceased; and perform a display propriety determination when a cessation determination is acquired, the cessation determination indicating a determination result that the detection of the region of interest has ceased, the display propriety determination being a determination of whether to display assisting information on the monitor apparatus, the assisting information being information for assisting to cause the region of interest, the detection of which has ceased, to be restored on a screen of the monitor apparatus. The processor outputs an image further including the assisting information to the monitor apparatus, as the image for display, when a determination to display the assisting information is made in the display propriety determination, and the processor outputs an image not including the assisting information to the monitor apparatus, as the image for display, when a determination not to display the assisting information is made in the display propriety determination.

An endoscopic image processing method according to one aspect of the present invention includes: acquiring an image of an object photographed by an endoscope; outputting an image for display including at least the acquired image to a monitor apparatus; detecting a region of interest included in the acquired image; determining whether a detection of the region of interest has ceased; and performing a display propriety determination when a cessation determination is acquired, the cessation determination indicating a determination result that the detection of the region of interest has ceased, the display propriety determination being a determination of whether to display assisting information on the monitor apparatus, the assisting information being information for assisting to cause the region of interest, the detection of which has ceased, to be restored on a screen of the monitor apparatus. An image further including the assisting information is outputted to the monitor apparatus, as the image for display, when a determination to display the assisting information is made in the display propriety determination, and an image not including the assisting information is outputted to the monitor apparatus, as the image for display, when a determination not to display the assisting information is made in the display propriety determination.

Furthermore, a recording medium according to one aspect of the present invention is a non-transitory computer readable recording medium configured to record a program to be run on by a computer, and the program causes the computer to execute: acquiring an image of an object photographed by an endoscope; outputting an image for display including at least the acquired image to a monitor apparatus; detecting a region of interest included in the acquired image; determining whether a detection of the region of interest has ceased; performing a display propriety determination when a cessation determination is acquired, the cessation determination indicating a determination result that the detection of the region of interest has ceased, the display propriety determination being a determination of whether to display assisting information on the monitor apparatus, the assisting information being information for assisting to cause the region of interest, the detection of which has ceased, to be restored on a screen of the monitor apparatus; outputting an image further including the assisting information to the monitor apparatus, as the image for display, when a determination to display the assisting information is made in the display propriety determination, and processing of outputting an image not including the assisting information to the monitor apparatus, as the image for display, when a determination not to display the assisting information is made in the display propriety determination.

DETAILED DESCRIPTION OF THE PREFERRED EMBODIMENTS

Hereinafter, embodiments of the present invention will be described with reference to drawings.

First Embodiment (Configuration of Endoscope System)

Figure 1:
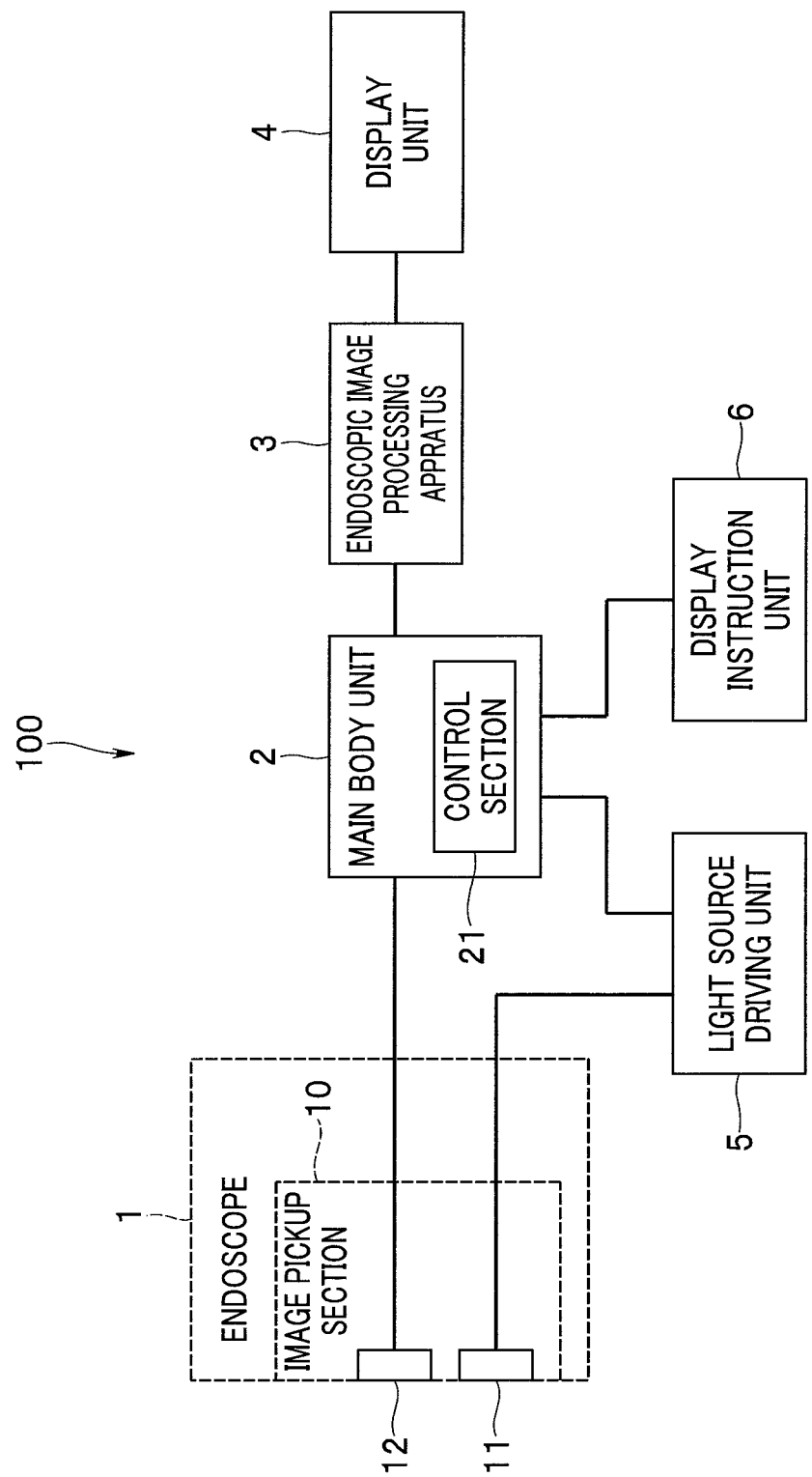
FIG. 1 is an explanatory diagram illustrating a schematic configuration of an endoscope system including an image processing apparatus according to a first embodiment of the present invention.

First, description will be made on a schematic configuration of an endoscope system including an endoscopic image processing apparatus according to the first embodiment of the present invention. FIG. 1 is an explanatory diagram illustrating a schematic configuration of an endoscope system 100. As illustrated in FIG. 1, the endoscope system 100 includes an endoscope 1, a main body unit 2, an endoscopic image processing apparatus (hereinafter, simply referred to as image processing apparatus) 3 according to the present embodiment, and a display unit 4, and a light source driving unit 5. The endoscope 1 is connected to the main body unit 2. The light source driving unit 5 is connected to the endoscope 1 and the main body unit 2. The main body unit 2 is connected to the image processing apparatus 3. The image processing apparatus 3 is connected to the display unit 4.

The endoscope 1 includes an insertion portion configured to be inserted into a subject. The insertion portion includes, at the distal end portion thereof, an image pickup section 10. The image pickup section 10 includes a light source section 11 and an image pickup device 12. The light source section 11 is configured by light-emitting elements such as LEDs, and generates illumination light to be applied to an object. Reflected light from the object irradiated with the illumination light is taken into the image pickup device 12 through an observation window, not illustrated. The image pickup device 12 is configured by a CCD or a CMOS, for example, and generates an image pickup signal by photoelectrically converting the reflected light from the object.

The image pickup signal generated by the image pickup device 12 is converted from an analog signal to a digital signal by an A/D converter, not illustrated, provided in the image pickup section 10. The image pickup section 10 outputs the digitally-converted image pickup signal to the main body unit 2.

The main body unit 2 is configured as a video processor, and includes a control section 21 configured to control the endoscope 1 and the light source driving unit 5 and perform predetermined image processing on the image pickup signal. The predetermined image processing includes, for example, image adjustments such as a gain adjustment, a white balance adjustment, a gamma correction, a contour enhancement correction, an enlargement/reduction adjustment, and the like. The control section 21 sequentially outputs image pickup signals subjected to the predetermined image processing, as observation images G1, to the image processing apparatus 3.

The light source driving unit 5 is a circuit for driving the light source section 11, and is connected to the light source section 11 of the endoscope 1 and the control section 21 of the main body unit 2. When receiving a control signal from the control section 21 of the main body unit 2, the light source driving unit 5 outputs a driving signal to the light source section 11 to drive the light source section 11 to cause the light source section 11 to generate illumination light.

The image processing apparatus 3 generates an image for display G based on an observation image G1 outputted from the control section 21 of the main body unit 2, to output the image for display G to the display unit 4. The display unit 4 is configured by a monitor apparatus and the like, and displays the image for display G outputted from the image processing apparatus 3 on a screen. The configuration of the image processing apparatus 3 will be described later.

The endoscope system 100 further includes a display instruction unit 6 connected to the main body unit 2. The display instruction unit 6 will be described later.

Figure 2:
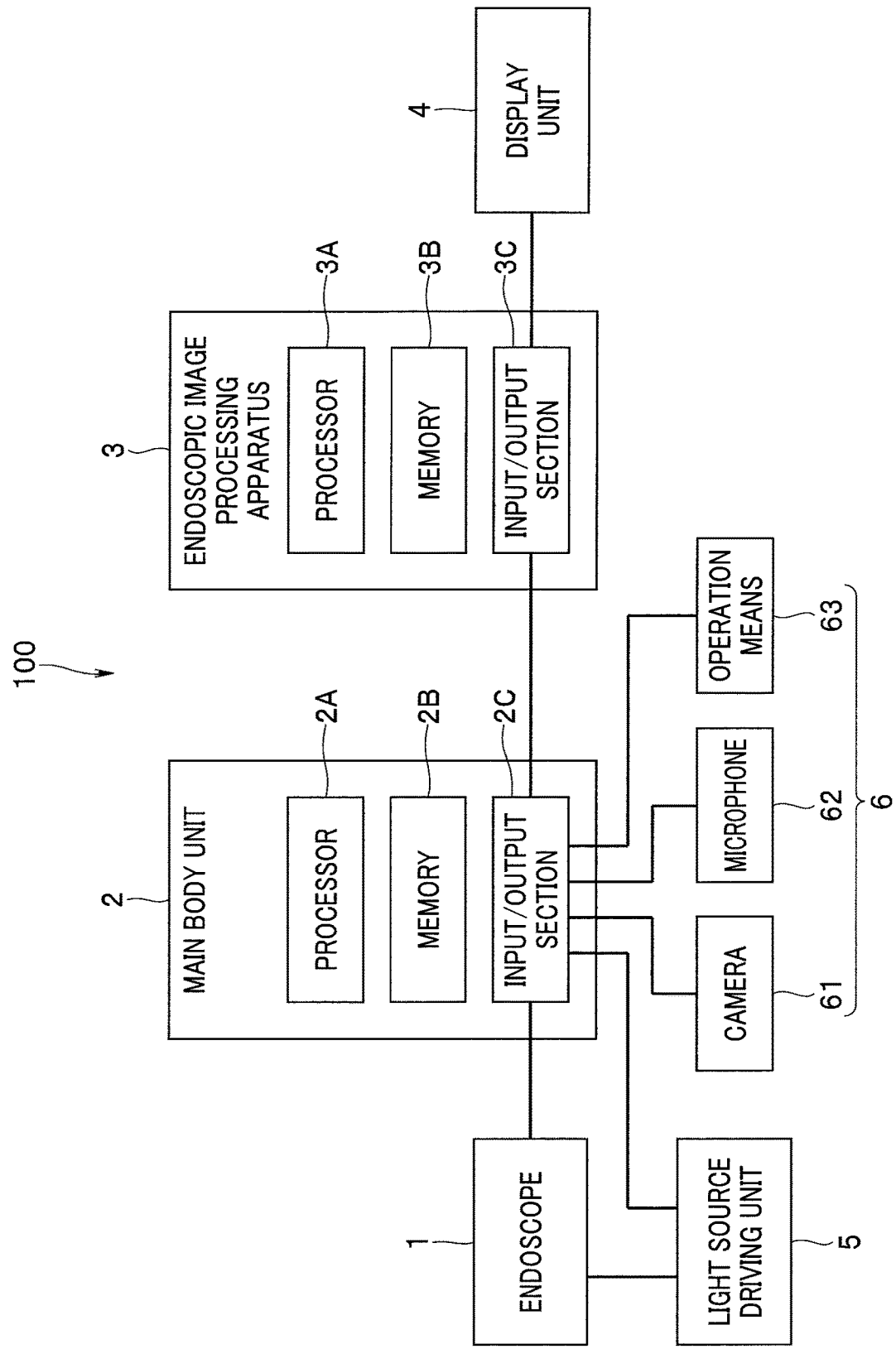
FIG. 2 is an explanatory diagram illustrating one example of hardware configurations of a main body unit and the image processing apparatus that are illustrated in FIG. 1.

Now, the hardware configurations of the main body unit 2 and the image processing apparatus 3 are described with reference to FIG. 2. FIG. 2 is an explanatory diagram illustrating one example of the hardware configurations of the main body unit 2 and the image processing apparatus 3. In the example illustrated in FIG. 2, the main body unit 2 is configured by a processor 2A, a memory 2B, and an input/ output section 2C. Furthermore, the image processing apparatus 3 is configured by a processor 3A, a memory 3B, and an input/output section 3C.

The processor 2A is used for executing a function of a constituent element such as the control section 21 of the main body unit 2. The processor 3A is used for executing functions of a plurality of constituent elements (except the storage section) of the image processing apparatus 3 to be described later. Each of the processors 2A and 3A is configured by an FPGA (Field Programmable Gate Array), for example. At least a part of the constituent elements of the main body unit 2, such as the control section 21, and at least a part of the plurality of constituent elements of the image processing apparatus 3 may be respectively configured as circuit blocks in the FPGA.

Each of the memories 2B and 3B is configured by a rewritable storage device such as a RAM, for example. The input/output section 2C is used for transmitting and receiving signals between the main body unit 2 and outside. The input/output section 3C is used for transmitting and receiving signals between the image processing apparatus 3 and outside.

Note that each of the processors 2A and 3A may be configured by a central processing unit (hereinafter, referred to as CPU). In this case, the function of the constituent element, such as the control section 21, of the main body unit 2 may be implemented by the CPU reading out a program from the memory 2B or a storage apparatus, not illustrated, and executing the program. Similarly, the function of each of the plurality of constituent elements of the image processing apparatus 3 may be implemented by the CPU reading out a program from the memory 3B or a storage apparatus, not illustrated, and executing the program.

The hardware configurations of the main body unit 2 and the image processing apparatus 3 are not limited to the example illustrated in FIG. 2. For example, the control section 21 and the respective constituent elements of the main body unit 2 other than the control section 21 may be configured as separate electronic circuits. The main body unit 2 and the image processing apparatus 3 may be configured as an integrated apparatus.

(Configuration of Image Processing Apparatus)

Figure 3:
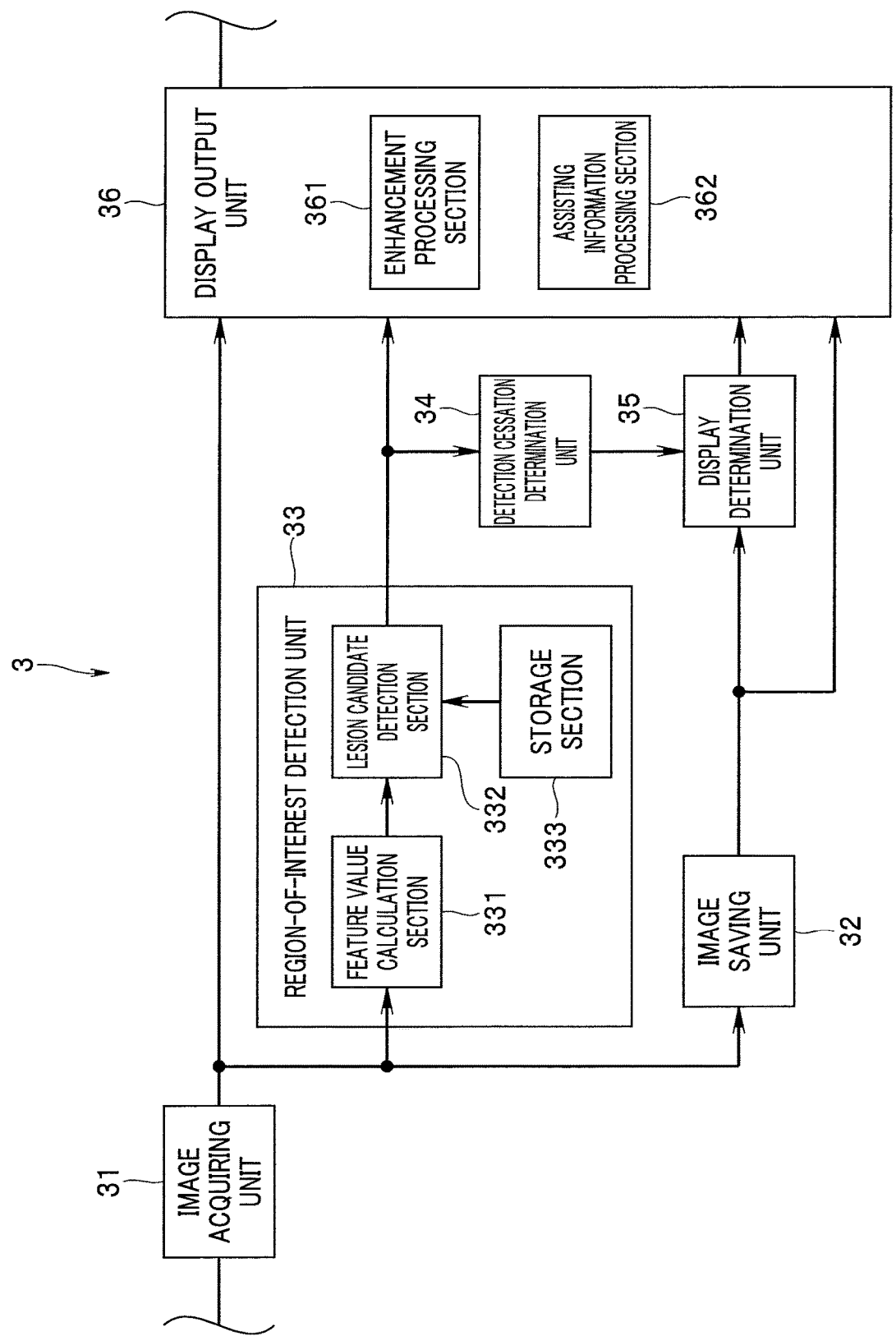
FIG. 3 is a functional block diagram illustrating a configuration of the image processing apparatus according to the first embodiment of the present invention.

Next, the configuration of the image processing apparatus 3 will be described with reference to FIG. 3. FIG. 3 is a functional block diagram illustrating the configuration of the image processing apparatus 3. The image processing apparatus 3 includes an image acquiring unit 31, an image saving unit 32, a region-of-interest detection unit 33, a detection cessation determination unit 34, a display determination unit 35, and a display output unit 36.

The image acquiring unit 31 acquires the observation image G1 outputted from the main body unit 2, as an image of the object photographed by the endoscope 1. In addition, the image acquiring unit 31 outputs the acquired observation image G1 to the image saving unit 32, the region-of-interest detection unit 33, and the display output unit 36.

The image saving unit 32 is configured to receive the observation image G1 acquired by the image acquiring unit 31. The image saving unit 32 is configured by at least one of the memory 3B illustrated in FIG. 2 or a storage apparatus, not illustrated, for example, and saves the observation image G1. The display output unit 36 is configured to be capable of reading out the observation image G1 saved in the image saving unit 32.

The region-of-interest detection unit 33 is configured to receive the observation image G1 acquired by the image acquiring unit 31. The region-of-interest detection unit 33 detects a region of interest included in the observation image G1. In addition, the region-of-interest detection unit 33 outputs the detection result of the region of interest to the detection cessation determination unit 34 and the display output unit 36. In the present embodiment, the region-of-interest detection unit 33 detects a lesion candidate region L as the region of interest. The detailed configuration of the region-of-interest detection unit 33 and a detection method of the lesion candidate region L will be described later.

The detection cessation determination unit 34 is configured to receive the detection result of the region-of-interest detection unit 33. The detection cessation determination unit 34 determines whether the detection of the region of interest in the region-of-interest detection unit 33 has ceased, based on the received detection result. The detection cessation determination unit 34 outputs the determination result to the display determination unit 35. Hereinafter, the determination result that the detection of the region of interest has ceased is referred to as the cessation determination. The determination method in the detection cessation determination unit 34 will be described later.

The display determination unit 35 is configured to receive the determination result of the detection cessation determination unit 34. When the cessation determination is acquired, the display determination unit 35 performs a display propriety determination to determine whether to display the assisting information on the display unit 4. The assisting information is for assisting to cause the region of interest, the detection of which has ceased, to be restored on the screen of the display unit 4. The display determination unit 35 outputs the result of the display propriety determination to the display output unit 36. The detailed configuration of the display determination unit 35 and the contents of the display propriety determination will be described later.

The display output unit 36 reads out the observation image G1 saved in the image saving unit 32, generates the image for display G including at least the observation image G1, and outputs the generated image for display G to the display unit 4. Note that the display output unit 36 may generate the image for display G using the observation image G1 outputted by the image acquiring unit 31 instead of using the observation image G1 saved in the image saving unit 32.

In addition, the display output unit 36 is configured to receive the result of the display propriety determination of the display determination unit 35. When it is determined to display the assisting information on the display unit 4 in the display propriety determination, the display output unit 36 generates an image including the assisting information as the image for display G and outputs the generated image to the display unit 4. On the other hand, when it is determined not to display the assisting information on the display unit 4 in the display propriety determination, the display output unit 36 generates an image not including the assisting information as the image for display G and outputs the generated image to the display unit 4. The detailed configuration of the display output unit 36 and the configuration of the image for display G will be described later.

(Configuration of Region-of-Interest Detection Unit)

Next, description will be made on the region-of-interest detection unit 33 with reference to FIG. 3. In the present embodiment, the region-of-interest detection unit 33 includes a feature value calculation section 331 and a lesion candidate detection section 332, and a storage section 333.

The storage section 333 is configured by the memory 3B illustrated in FIG. 2 or by a storage apparatus, not illustrated, for example.

The feature value calculation section 331 is configured to receive the observation image G1 acquired by the image acquiring unit 31. The feature value calculation section 331 calculates the feature values of the pixels included in the observation image G1 and outputs the calculated feature values to the lesion candidate detection section 332. The feature values are calculated, for each of predetermined small regions on the observation image G1, for example, by calculating a change amount between pixels in each of the predetermined small regions and pixels adjacent to the pixels in each of the predetermined small regions, that is, a gradient value.

The lesion candidate detection section 332 is configured to receive the feature values calculated by the feature value calculation section 331. The lesion candidate detection section 332 detects the lesion candidate region L in the observation image G1 based on the feature values, and outputs the detection result of the lesion candidate region L, more specifically, lesion candidate information including information on a position, a size, and the like of the lesion candidate region L to the detection cessation determination unit 34 and the display output unit 36.

Note that the configuration of the region-of-interest detection unit 33 is not limited to the above-described example. For example, the region-of-interest detection unit 33 may be configured to detect the lesion candidate region L as the region of interest by a method of machine learning such as deep learning.

(Detection Method of Lesion Candidate Region)

Hereinafter, description will be made on the detection method of the lesion candidate region L in the lesion candidate detection section 332. The detection of the lesion candidate region L is performed by comparing the feature values with lesion model information. The lesion model information includes the feature values of the features commonly included in many lesion images. The storage section 333 stores a plurality of pieces of lesion model information in advance. The lesion candidate detection section 332 reads out the plurality of pieces of lesion model information from the storage section 333 and compares the received feature values with the plurality of lesion model information, to detect the lesion candidate region L.

Specifically, the lesion candidate detection section 332 compares the feature values for each of the predetermined small regions, which are received from the feature value calculation section, with the lesion model information, for example, and detects a region where the feature values received from the feature value calculation section and the feature values in the lesion model information coincide with each other, as the lesion candidate region L.

(Determination Method in Detection Cessation Determination Unit)

Next, description will be made on the determination method in the detection cessation determination unit 34. As described above, the detection cessation determination unit 34 determines whether the detection of the region of interest in the region-of-interest detection unit 33 has ceased, based on the detection result of the region-of-interest detection unit 33. The determination on whether the detection of the region of interest has ceased is performed by monitoring whether the region of interest is continuously detected in the region-of-interest detection unit 33. When the region of interest is continuously detected, the detection cessation determination unit 34 determines that the detection of the region of interest in the region-of-interest detection unit 33 does not cease. On the other hand, the detection of the region of interest has ceased, the detection cessation determination unit 34 determines that the detection of the region of interest in the region-of-interest detection unit 33 has ceased.

Hereinafter, one example of the specific determination method will be described by taking the lesion candidate region L as an example. The detection cessation determination unit 34 is configured to receive the lesion candidate information including the position, the size, and the like of the lesion candidate region L, as the detection result of the region-of-interest detection unit 33. The detection cessation determination unit 34 first uses the lesion candidate information detected from the present observation image G1 (hereinafter, referred to as first lesion candidate information) and the lesion candidate information detected from a past observation image G1, for example, the observation image G1 which is an image of one frame before the frame of the present observation image G1 (hereinafter, referred to as second lesion candidate information), to determine whether the lesion candidate region L indicated by the first lesion candidate information and the lesion candidate region L indicated by the second lesion candidate information are the same. The determination on whether the two lesion candidate regions L are the same is performed based on the overlapping state of the two lesion candidate regions L, for example. When the two lesion candidate regions L are determined to be the same, the detection cessation determination unit 34 determines that the detection of the lesion candidate region L does not cease.

On the other hand, when the two lesion candidate regions L are determined not to be the same, the detection cessation determination unit 34 determines that the detection of the lesion candidate region L indicated by the second lesion candidate information has ceased. Furthermore, also when the first lesion candidate information is not acquired, the detection cessation determination unit 34 determines that the detection of the lesion candidate region L indicated by the second lesion candidate information has ceased.

Note that the detection cessation determination unit 34 may include a storage section, not illustrated, configured to store the second lesion candidate information. The storage section, not illustrated, is configured by the memory 3B illustrated in FIG. 2 or the storage apparatus not illustrated, for example.

(Configuration of Display Determination Unit)

Figure 4:
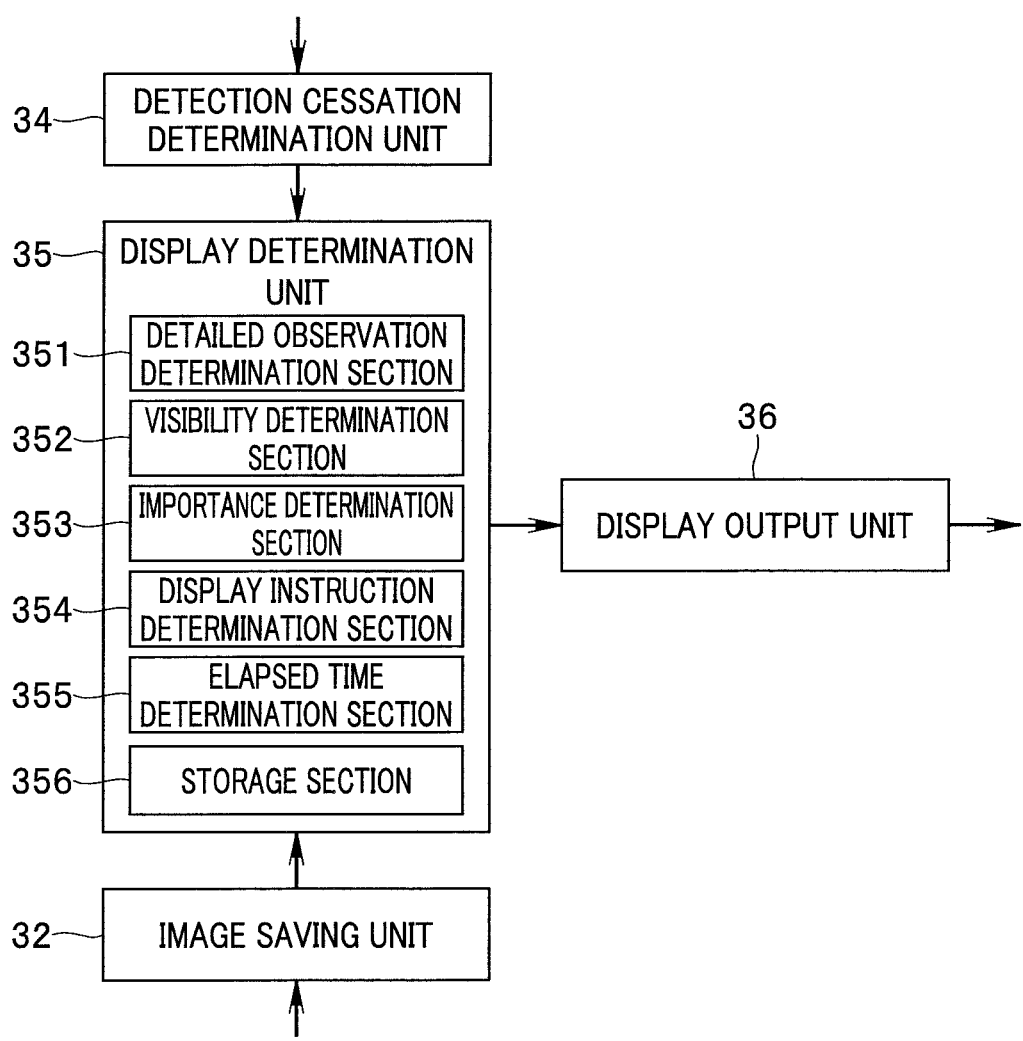
FIG. 4 is a functional block diagram illustrating a configuration of a display determination unit in the first embodiment of the present invention.

Next, description will be made on the display determination unit 35 with reference to FIG. 4. FIG. 4 is a functional block diagram illustrating the configuration of the display determination unit 35. The display determination unit 35 includes a plurality of determination sections each configured to perform a display propriety determination when the cessation determination is acquired. In the present embodiment, the display determination unit 35 includes a detailed observation determination section 351, a visibility determination section 352, an importance determination section 353, a display instruction determination section 354, an elapsed time determination section 355, and a storage section 356. The storage section 356 is configured by the memory 3B illustrated in FIG. 2 or by the storage apparatus, not illustrated, for example.

The detailed observation determination section 351 calculates a detailed observation parameter that changes depending on whether the lesion candidate region L as the region of interest is observed in detail, and performs a display propriety determination based on the calculated detailed observation parameter. The detailed observation parameter is defined so as to become a larger value as it becomes more likely that the user of the endoscope 1 has observed the lesion candidate region L in detail, for example.

In the present embodiment, the detailed observation parameter is calculated based on at least one of the shape change amount of the lesion candidate region L, the moving amount of the lesion candidate region L, or an observation mode of the endoscope 1. The shape change amount of the lesion candidate region L and the moving amount of the lesion candidate region L can be calculated by using a plurality of pieces of lesion candidate information corresponding to the lesion candidate region L, the detection of which is determined to have ceased. When the shape change amount and the moving amount are small, it is more likely that the user has observed the lesion candidate region L. Therefore, in such a case, the detailed observation parameter is calculated to be a large value.

Note that the storage section 356 is configured to store the lesion candidate information. The detailed observation determination section 351 may read, from the storage section 356, a plurality pieces of lesion candidate information corresponding to the lesion candidate region L, the detection of which is determined to have ceased, to calculate the shape change amount of the lesion candidate region L and the moving amount of the lesion candidate region L.

The observation mode of the endoscope 1 can be specified by any operation means such as an operation button, an operation switch, or the like, for example. As the operation means, the operation means 63 illustrated in FIG. 2 can be used, for example. The operation means 63 is connected to the input/output section 2C of the main body unit 2. The control section 21 of the main body unit 2 outputs information on the observation mode of the endoscope 1 to the image processing apparatus 3. The detailed observation determination section 351 is configured to receive the information on the observation mode of the endoscope 1 outputted from the control section 21. When the lesion candidate region L, the detection of which is determined to have ceased, is detected from the observation image G1 acquired when the narrow-band light observation (Narrow Band Imaging) mode or the mode in which observation is performed by dyeing the inside of the subject is selected, for example, it is more likely that the user has observed the lesion candidate region L in detail. Therefore, in such a case, the detailed observation parameter is calculated to be a large value.

The visibility determination section 352 calculates a visibility parameter that changes depending on an easiness of visual recognition of the lesion candidate region L as the region of interest, and performs a display propriety determination based on the calculated visibility parameter. The easier the visual recognition of the lesion candidate region L, the larger the visibility parameter is defined, for example.

In the present embodiment, the visibility parameter is calculated based on at least one of the color, the shape, or the texture of the lesion candidate region L. The color, the shape, and the texture of the lesion candidate region L can be acquired from the information on the position, the size, and the like of the lesion candidate region L, the detection of which is determined to have ceased, and the observation image G1 in which the lesion candidate region L has been detected, for example. The more characteristic the color, the shape, and the texture of the lesion candidate region L, the easier the visual recognition of the lesion candidate region L. Therefore, the visibility parameter is calculated to be a large value, when the color, the shape, and the texture of the lesion candidate region L are characteristic.

Note that the storage section 356 is configured to store the lesion candidate information, as described above. The visibility determination section 352 may read out, from the storage section 356, the lesion candidate information corresponding to the lesion candidate region L, the detection of which is determined to have ceased, and may read out, from the image saving unit 32, the observation image G1 from which the lesion candidate information has been detected, to acquire the color, the shape, and the texture of the lesion candidate region L.

The importance determination section 353 calculates the medical importance of the lesion candidate region L as the region of interest, and performs a display propriety determination based on the calculated importance. In the present embodiment, in particular, the importance determination section 353 performs the display propriety determination based on the importance parameter having correspondence with the importance. The importance parameter is specified to be a smaller value as the importance becomes higher, that is, the medical danger becomes higher, and to be a larger value as the importance becomes lower, that is the medical danger becomes lower.

The importance is calculated based on at least one of the color, the shape, or the texture of the lesion candidate region L. The importance determination section 353 may read out, from the storage section 356, the lesion candidate information corresponding to the lesion candidate region L, the detection of which is determined to have ceased, and may read out, from the image saving unit 32, the observation image G1 from which the lesion candidate information has been detected, to acquire the color, the shape, and the texture of the lesion candidate region L.

When the cessation determination is acquired, the display instruction determination section 354 performs a display propriety determination based on the instruction of whether to display the assisting information by the user of the endoscope 1. The instruction of whether to display the assisting information is acquired through the display instruction unit 6 illustrated in FIG. 1, for example. The control section 21 of the main body unit 2 outputs the contents of the acquired instruction to the image processing apparatus 3. The contents of the instruction outputted from the control section 21 is inputted to the display instruction determination section 354.

In the present embodiment, the instruction of whether to display the assisting information is given by at least one of the line of sight of the user, utterance of the user, or operation of the instruction means by the user. As illustrated in FIG. 2, the display instruction unit 6 includes, for example, a camera 61 configured to detect the line of sight of the user, a microphone 62 configured to detect the utterance of the user, and the operation means 63 such as an operation button, an operation switch, and the like, as the instruction means.

Note that the display instruction unit 6 may be connected to the image processing apparatus 3. In this case, the display instruction determination section 354 may acquire the contents of the instruction directly from the display instruction unit 6. Note that, in this case, the camera 61, the microphone 62, and the operation means 63 that are illustrated in FIG. 2 are connected to the input/output section 3C of the image processing apparatus 3.

The elapsed time determination section 355 measures the elapsed time from the time point of the acquisition of the cessation determination, and performs a display propriety determination based on the measured elapsed time.

The display determination unit 35 decides the contents of the determination result to be outputted to the display output unit 36, based on the determination result of each of the detailed observation determination section 351, the visibility determination section 352, the importance determination section 353, the display instruction determination section 354, and the elapsed time determination section 355, and outputs the decided determination result to the display output unit 36.

Here, description is made on the method of deciding the contents of the determination result. The contents of the determination result are decided as described below, for example. First, the parameters used respectively for the display propriety determinations in the detailed observation determination section 351, the visibility determination section 352, the importance determination section 353, and the elapsed time determination section 355 are standardized to calculate four standardized parameters. These standardized parameters are set so as to become 1 when there is a highest possibility that the assisting information is determined not to be displayed, and become 0 when there is a highest possibility that the assisting information is determined to be displayed, for example. In addition, the instruction used for the display propriety determination in the display instruction determination section 354 is converted into a numerical value as a standardized parameter. The standardized parameter is 1 when the instruction not to display the assisting information is given, and 0 when the instruction to display the assisting information is given. The contents of the determination result are decided based on the standardized parameter having the largest value among the above-described five standardized parameters.

Specifically, comparison is made between the standardized parameter having the largest value and a predetermined threshold (a value larger than 0 and smaller than 1), for example. When the standardized parameter having the largest value is equal to or larger than the predetermined threshold, the display determination unit 35 decides the determination result to be outputted to the display output unit 36 so as to have the contents indicative of a non-display of the assisting information. On the other hand, the standardized parameter having the largest value is smaller than the predetermined threshold, the display determination unit 35 decides the determination result to be outputted to the display output unit 36 so as to have the contents indicative of a display of the assisting information.

Note that the method of deciding the contents of the determination result is not limited to the above-described method. For example, the five standardized parameters may be weight-averaged, and the contents of the determination result may be decided based on the weight-averaged standardized parameter.

In addition, the configuration of the display determination unit 35 is not limited to the example illustrated in FIG. 4. For example, the display determination unit 35 may include only some of the plurality of determination sections illustrated in FIG. 4, or may include a determination section other than the plurality of determination sections illustrated in FIG. 4.

(Contents of Display Propriety Determination)

Next, description will be made on the contents of the display propriety determination that is performed in each of the detailed observation determination section 351, the visibility determination section 352, the importance determination section 353, the display instruction determination section 354, and the elapsed time determination section 355.

Figure 5:
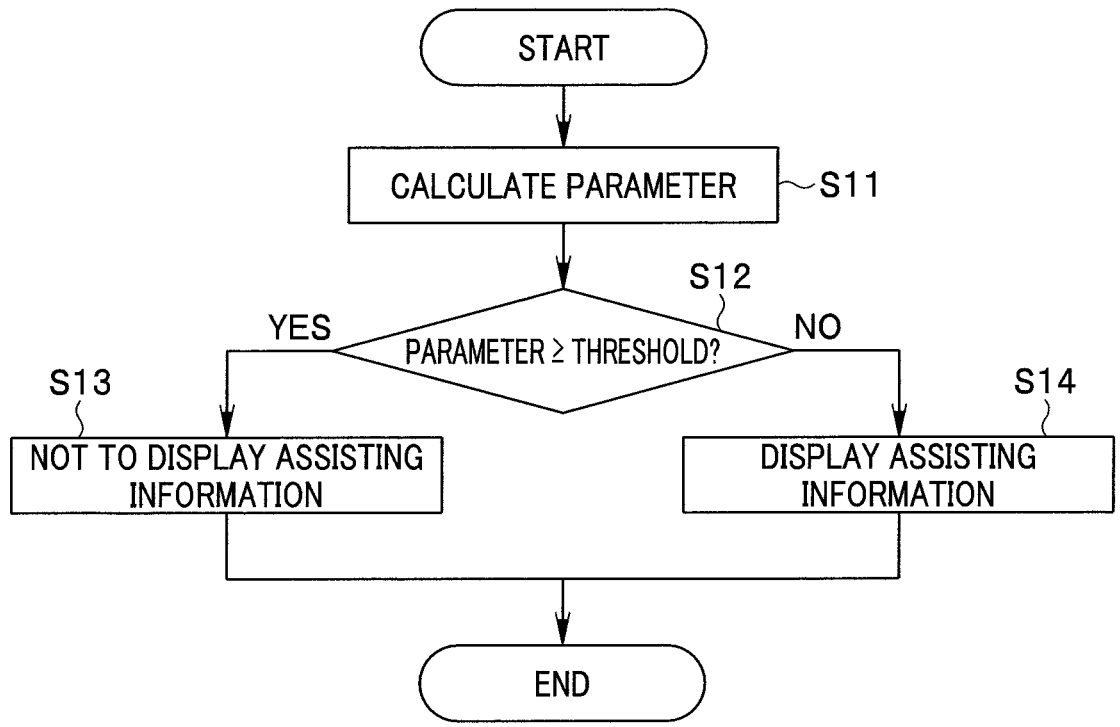
FIG. 5 is a flowchart illustrating a display propriety determination that is performed in each of a detailed observation determination section, a visibility determination section, an importance determination section, and an elapsed time determination section in the first embodiment of the present invention.

First, description will be made on the display propriety determination that is performed in the detailed observation determination section 351, with reference to FIG. 5. FIG. 5 is a flowchart illustrating the display propriety determination that is performed in each of the detailed observation determination section 351, the visibility determination section 352, the importance determination section 353, and the elapsed time determination section 355.

When the cessation determination is acquired, the detailed observation determination section 351 first calculates the detailed observation parameter (step S11). Next, the detailed observation determination section 351 compares the detailed observation parameter with the predetermined threshold (step S12). When the detailed observation parameter is equal to or larger than the predetermined threshold (YES), the detailed observation determination section 351 determines not to display the assisting information (step S13). On the other hand, when the detailed observation parameter is smaller than the predetermined threshold (NO), the detailed observation determination section 351 determines to display the assisting information (step S14). The steps S12, S13, and S14 illustrated in FIG. 5 correspond to the display propriety determination that is performed in the detailed observation determination section 351.

Note that the case where the detailed observation parameter is equal to or larger than the predetermined threshold corresponds to the case where it is estimated that the lesion candidate region L is observed in detail. The case where the detailed observation parameter is smaller than the predetermined threshold corresponds to the case where it is estimated that the lesion candidate region L is not observed in detail.

The contents of the display propriety determination that is performed in each of the visibility determination section 352, the importance determination section 353, and the elapsed time determination section 355 are basically the same as those of the display propriety determination that is performed in the detailed observation determination section 351. That is, when the cessation determination is acquired, the visibility determination section 352 first calculates the visibility parameter (step S11). Next, the visibility determination section 352 compares the visibility parameter with the predetermined threshold (step S12). When the visibility parameter is equal to or larger than the predetermined threshold (YES), the visibility determination section 352 determines not to display the assisting information (step S13). On the other hand, when the visibility parameter is smaller than the predetermined threshold (NO), the visibility determination section 352 determines to display the assisting information (step S14). The steps S12, S13, and S14 illustrated in FIG. 5 correspond to the display propriety determination that is performed in the visibility determination section 352.

Note that the case where the visibility parameter is equal to or larger than the predetermined threshold corresponds to the case where the lesion candidate region L is easy to visually recognize. The case where the visibility parameter is smaller than the predetermined threshold corresponds to the case where the lesion candidate region L is hard to visually recognize.

Furthermore, when the cessation determination is acquired, the importance determination section 353 first calculates importance, and then calculates the importance parameter having correspondence with the importance (step S11). Next, the importance determination section 353 compares the importance parameter with the predetermined threshold (step S12). When the importance parameter is equal to or larger than the predetermined threshold (YES), that is, the importance is low, the importance determination section 353 determines not to display the assisting information (step S13). On the other hand, when the importance parameter is smaller than the predetermined threshold (NO), that is, the importance is high, the importance determination section 353 determines to display the assisting information (step S14). The steps S12, S13, and S14 illustrated in FIG. 5 correspond to the display propriety determination that is performed in the importance determination section 353.

Furthermore, when the cessation determination is acquired, the elapsed time determination section 355 first measures the elapsed time from the time point of the acquisition of the cessation determination. The elapsed time corresponds to the parameter in the step S11 in FIG. 5. Next, the elapsed time determination section 355 compares the elapsed time with the predetermined threshold (step S12). When the elapsed time is equal to or larger than the predetermined threshold (YES), the elapsed time determination section 355 determines not to display the assisting information (step S13). On the other hand, when the elapsed time is smaller than the predetermined threshold (NO), the elapsed time determination section 355 determines to display the assisting information (step S14). The steps S12, S13, and S14 illustrated in FIG. 5 correspond to the display propriety determination that is performed in the elapsed time determination section 355. Note that the display propriety determination that is performed in the elapsed time determination section 355 may be repeatedly performed after the cessation determination, at predetermined time intervals, for example.

Figure 6:
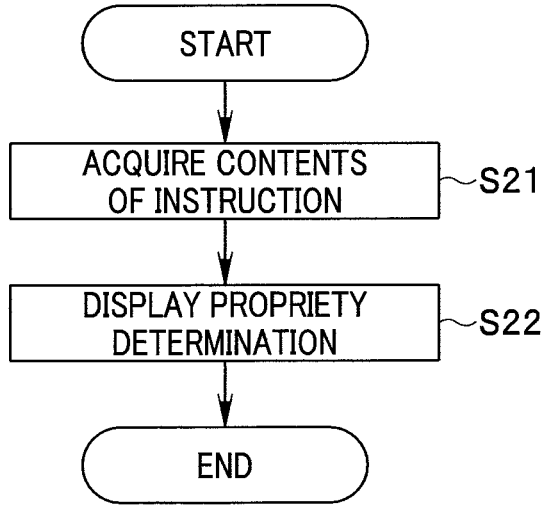
FIG. 6 is a flowchart illustrating a display propriety determination that is performed in a display instruction determination section in the first embodiment of the present invention.

Next, description will be made on the display propriety determination that is performed in the display instruction determination section 354, with reference to FIG. 6. FIG. 6 is a flowchart illustrating the display propriety determination that is performed in the display instruction determination section 354. When the cessation determination is acquired, the display instruction determination section 354 first acquires the contents of the instruction of whether to display the assisting information (step S21). Next, the display instruction determination section 354 performs the display propriety determination based on the contents of the acquired instruction (step S22). When the contents of the acquired instruction indicate the non-display of the assisting information, the display instruction determination section 354 determines not to display the assisting information. When the contents of the acquired instruction indicate the display of the assisting information, the display instruction determination section 354 determines to display the assisting information. Note that the display propriety determination that is performed in the display instruction determination section 354 may be repeatedly performed after the cessation determination, at predetermined time intervals, for example.

(Configuration of Display Output Unit)

Next, description will be made on the configuration of the display output unit 36, with reference to FIG. 3. In the present embodiment, the display output unit 36 includes an enhancement processing section 361 and an assisting information processing section 362. The display output unit 36 is capable of performing enhancement processing and assisting information display processing based on the observation image G1 read out from the image saving unit 32, the detection result of the lesion candidate region L, i.e., the lesion candidate information inputted from the lesion candidate detection section 332, and the determination result inputted from the display determination unit 35.

The enhancement processing section 361 performs enhancement processing on the observation image G1 when the lesion candidate region L is detected in the lesion candidate detection section 332. The enhancement processing is processing for displaying the position of the lesion candidate region L in an enhanced manner. Specifically, the enhancement processing section 361 may perform the following processing, as the enhancement processing, on the observation image G1. For example, the enhancement processing section 361 may perform processing for adding a marker image surrounding the lesion candidate region L or processing for making the brightness and the color tone of the lesion candidate region L different from those of peripheral regions.

The assisting information processing section 362 performs the assisting information display processing on the observation image G1, when the determination result inputted from the display determination unit 35 includes the contents indicating the display of the assisting information. The assisting information display processing is processing for performing display showing the position of the lesion candidate region L when the lesion candidate region L as the region of interest has disappeared from the screen of the display unit 4. Specifically, the assisting information processing section 362 may perform the following processing, as the assisting information display processing, on the observation image G1. For example, the assisting information processing section 362 may perform processing for adding an alert image indicating the position and the direction of the disappeared lesion candidate region L, or processing for changing the color of the outer frame of the observation image G1.

When the lesion candidate region L is detected in the lesion candidate detection section 332 and the determination result inputted from the display determination unit 35 includes the contents indicating the display of the assisting information, the display output unit 36 outputs the image described below, as the image for display G, to the display unit 4. That is, the display output unit 36 outputs to the display unit 4 the observation image G1 subjected to the enhancement processing and the assisting information display processing, i.e., the image including the display showing the position of the lesion candidate region L in an enhanced manner and the display showing the position of the lesion candidate region L as the assisting information (see FIG. 1).

When the lesion candidate region L is not detected in the lesion candidate detection section 332 and the determination result inputted from the display determination unit 35 includes the contents indicating the display of the assisting information, the display output unit 36 outputs the image described below, as the image for display G, to the display unit 4. That is, the display output unit 36 outputs to the display unit 4 the observation image G1 not subjected to the enhancement processing but subjected to the assisting information display processing, i.e., the image including the display showing the position of the lesion candidate region L as the assisting information but not including the display showing the position of the lesion candidate region L in an enhanced manner.

When the lesion candidate region L is not detected in the lesion candidate detection section 332 and the determination result inputted from the display determination unit 35 includes the contents indicating the non-display of the assisting information, the display output unit 36 outputs the image described below, as the image for display G, to the display unit 4. That is, the display output unit 36 outputs to the display unit 4 the observation image G1 subjected to neither the enhancement processing nor the assisting information display processing, i.e., the image including neither the display showing the position of the lesion candidate region L in an enhanced manner nor the display showing the position of the lesion candidate region L as the assisting information.

(Configuration of Image for Display)

Figure 7:
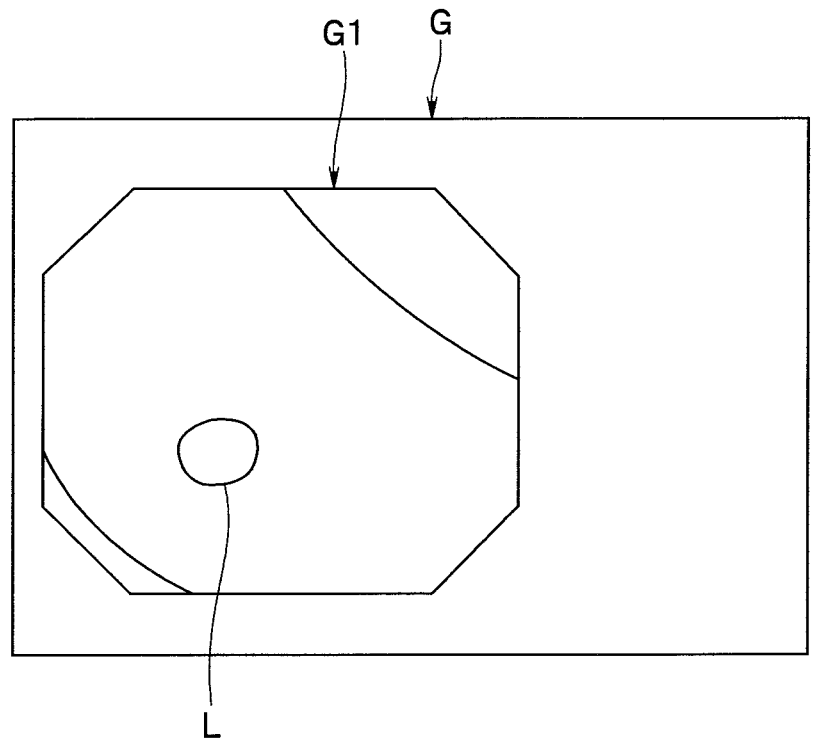
FIG. 7 is an explanatory diagram illustrating one example of an image for display in the first embodiment of the present invention.

Next, description will be made on the configuration of the image for display G. FIG. 7 is an explanatory diagram illustrating one example of the configuration of the image for display G. As illustrated in FIG. 7, the observation image G1 is disposed on the image for display G outputted from the display output unit 36. FIG. 7 illustrates, as one example of the observation image G1, an inner wall of a colon including the lesion candidate region L.

Figure 8:
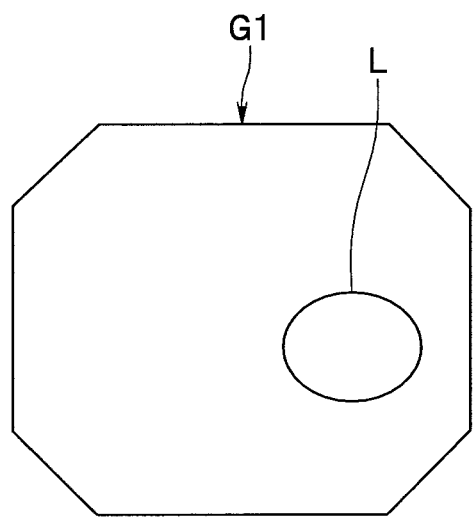
FIG. 8 is an explanatory diagram illustrating a first example of an observation image in the first embodiment of the present invention.
Figure 10:
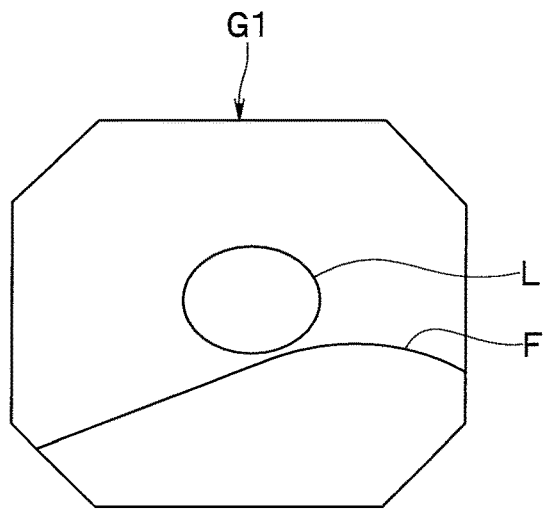
FIG. 10 is an explanatory diagram illustrating a second example of the observation image in the first embodiment of the present invention.

Here, description is made on a first example and a second example of the assisting information display processing to be performed on the observation image G1. FIG. 8 is an explanatory diagram illustrating the first example of the observation image G1. FIG. 10 is an explanatory diagram illustrating the second example of the observation image G1.

As illustrated in FIG. 8, the lesion candidate region L is displayed on the observation image G1.

Figure 9:
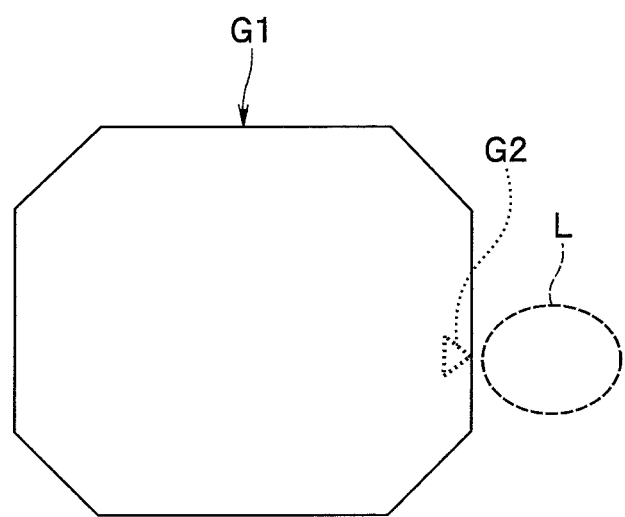
FIG. 9 is an explanatory diagram illustrating a state where a region of interest has disappeared from the observation image illustrated in FIG. 8.

FIG. 9 illustrates the state where the lesion candidate region L as the region of interest has disappeared from the observation image G1 illustrated in FIG. 8. FIG. 9 illustrates, in particular, the example in which the lesion candidate region L has moved to the outside of the outer edge of the observation image G1. In this state, the lesion candidate region L is not displayed on the screen of the display unit 4. When performing the assisting information display processing on the observation image G1, the assisting information processing section 362 adds an alert image G2 to the observation image G1. FIG. 9 illustrates the example in which the image is added as the alert image G2. In the added image, the position and the direction of the lesion candidate region L are indicated by the vertex of the triangle. Note that the alert image G2 may be another image such as an arrow.

FIG. 10 is an explanatory diagram illustrating the second example of the observation image G1. As illustrated in FIG. 10, the lesion candidate region L is displayed in the vicinity of the folds F on the observation image G1.

Figure 11:
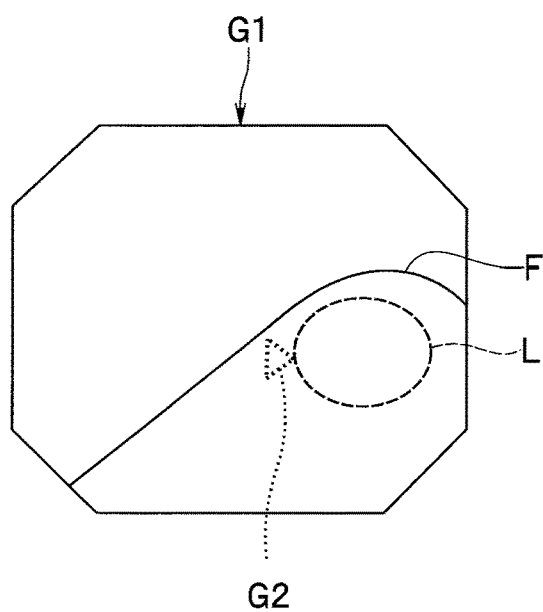
FIG. 11 is an explanatory diagram illustrating a state where the region of interest has disappeared from the observation image illustrated in FIG. 10.

FIG. 11 illustrates the state where the lesion candidate region L has disappeared from the observation image G1 illustrated in FIG. 10. FIG. 11 illustrates, in particular, the example in which the lesion candidate region L is hidden in the back side of the folds F. In this state, the lesion candidate region L is not displayed on the screen of the display unit 4. When performing the assisting information display processing on the observation image G1, the assisting information processing section 362 adds the alert image G2 to the observation image G1. FIG. 9 illustrates the example in which the image is added as the alert image G2. In the added image, the position and direction in which the lesion candidate region L hidden in the back side of the folds F is estimated to exist are indicated by the vertex of the triangle.

Note that, when not performing the assisting information display processing on the observation image G1, that is, the determination result inputted from the display determination unit 35 includes the contents indicating the non-display of the assisting information, the assisting information processing section 362 does not add the alert image G2 to the observation image G1.

(Working and Effect)

Next, a working and an effect of the image processing apparatus 3 according to the present embodiment will be described. In the present embodiment, when the cessation determination is acquired, the display determination unit 35 performs the display propriety determination as the determination of whether to display the assisting information on the display unit 4. With such a configuration, the present embodiment enables appropriate display of the assisting information. Specifically, as described above, when it is determined to display the assisting information in the display propriety determination, the display output unit 36 outputs to the display unit 4 the image further including the assisting information, as the image for display G. On the other hand, when it is determined not to display the assisting information in the display propriety determination, the display output unit 36 outputs to the display unit 4 the image not including the assisting information, as the image for display G. Hereinafter, the effect of the present embodiment will be described in detail.

In the case where the lesion candidate region L as the region of interest has disappeared from the screen of the display unit 4, when the detailed observation on the lesion candidate region L is finished, it is preferable not to display the assisting information in order to reduce the burden on the user of the endoscope 1 and prevent another lesion candidate region L from being hidden by the assisting information. In the present embodiment, the display determination unit 35 includes the detailed observation determination section 351. When it is estimated that the lesion candidate region L is observed in detail based on the detailed observation parameter, the detailed observation determination section 351 determines not to display the assisting information. On the other hand, when it is estimated that the lesion candidate region L is not observed in detail based on the detailed observation parameter, the detailed observation determination section 351 determines to display the assisting information. With such a configuration, the present embodiment enables appropriate display of the assisting information.

If the disappeared lesion candidate region L is easy to visually recognize, there is a possibility that detailed observation on the lesion candidate region L has been finished. On the other hand, if the disappeared lesion candidate region L is hard to visually recognize, there is a possibility that the lesion candidate region L is overlooked. In the present embodiment, the display determination unit 35 includes the visibility determination section 352. Based on the visibility parameter, in the case where the lesion candidate region L is easy to visually recognize, the visibility determination section 352 determines not to display the assisting information, while in the case where the lesion candidate region L is hard to visually recognize, the visibility determination section 352 determines to display the assisting information. With such a configuration, the present embodiment enables appropriate display of the assisting information.

When the importance of the disappeared lesion candidate region L is low, the necessity for causing the disappeared lesion candidate region L to be restored and observing the restored lesion candidate region L is low. However, when the importance of the disappeared lesion candidate region L is high, it is preferable to cause the disappeared lesion candidate region L to be restored and observe the restored lesion candidate region L in detail. In the present embodiment, the display determination unit 35 includes the importance determination section 353. When the importance of the lesion candidate region L is low, the importance determination section 353 determines not to display the assisting information. On the other hand, when the importance of the lesion candidate region L is high, the importance determination section 353 determines to display the assisting information.

With such a configuration, the present embodiment enables appropriate display of the assisting information.

Furthermore, in the present embodiment, the display determination unit 35 includes the display instruction determination section 354. The display instruction determination section 354 performs the display propriety determination based on the instruction of whether to display the assisting information by the user of the endoscope 1. That is, according to the present embodiment, selection of whether to display the assisting information can be made by a direct instruction. With such a configuration, the present embodiment enables appropriate display of the assisting information.

In addition, when the time elapsed from the disappearance of the lesion candidate region L is sufficiently long, it is more likely that the user does not have an intention to cause the disappeared lesion candidate region L to be restored and observe the restored lesion candidate region L. In the present embodiment, the display determination unit 35 includes the elapsed time determination section 355. The elapsed time determination section 355 determines not to display the assisting information when the time elapsed from the disappearance of the lesion candidate region L is relatively long. With such a configuration, the present embodiment enables appropriate display of the assisting information.

In the display propriety determination that is performed by each of the determination sections other than the display instruction determination section 354, selection of whether to display the assisting information is automatically made even if no instruction is given by the user. With such a configuration, the present embodiment is capable of reducing the burden on the user.

Second Embodiment (Configuration of Image Processing Apparatus)

Figure 12:
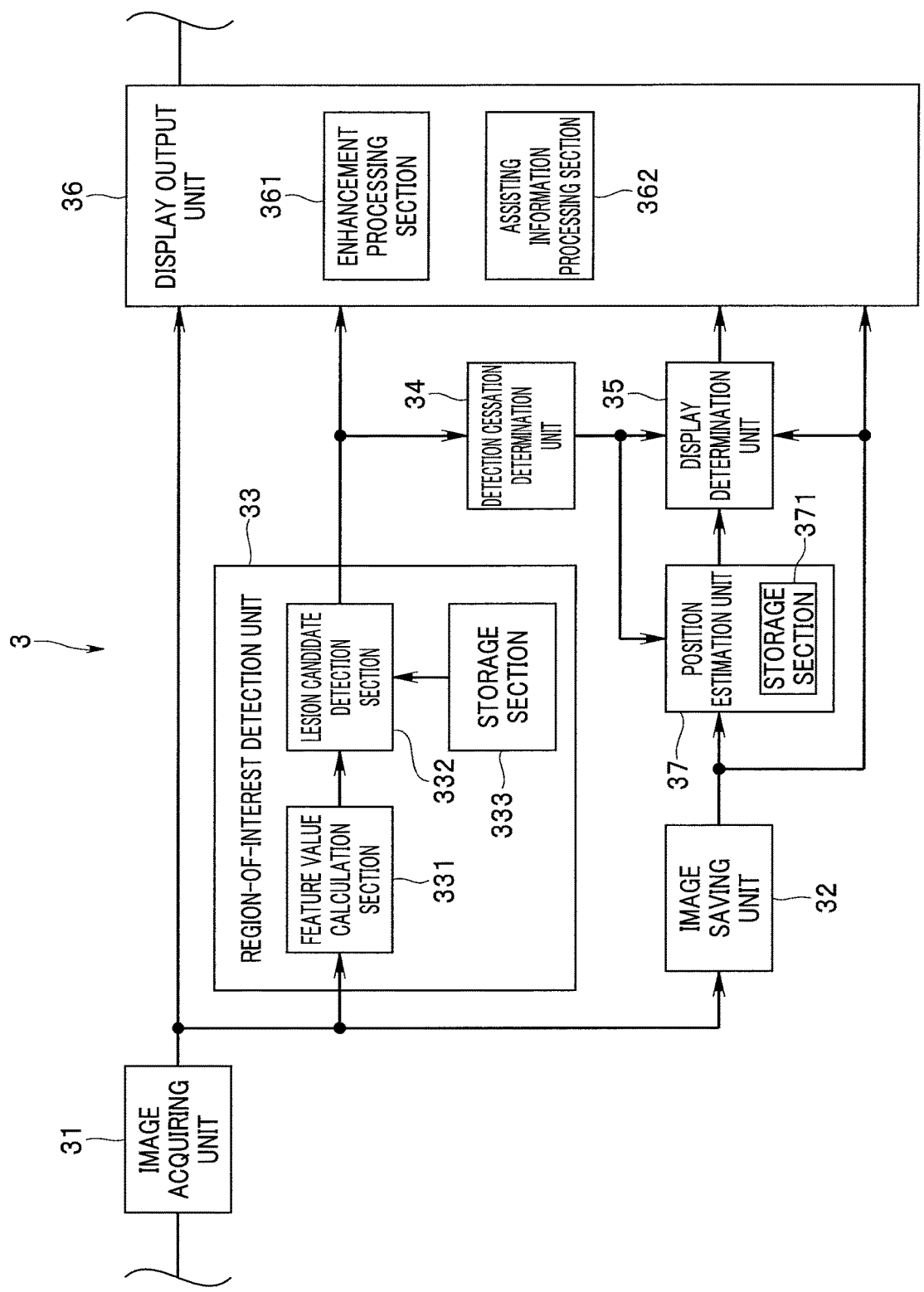
FIG. 12 is a functional block diagram illustrating a configuration of an image processing apparatus according to a second embodiment of the present invention.

Next, description will be made on an image processing apparatus according to the second embodiment of the present invention. FIG. 12 is a functional block diagram illustrating the configuration of the image processing apparatus according to the present embodiment. The image processing apparatus 3 according to the present embodiment includes a position estimation unit 37. The position estimation unit 37 includes a storage section 371. The storage section 371 is configured by the memory 3B illustrated in FIG. 2 in the first embodiment or by the storage apparatus, not illustrated, for example.

The position estimation unit 37 is configured to receive the determination result of the detection cessation determination unit 34. The position estimation unit 37 is configured to be capable of reading out the observation image G1 saved in the image saving unit 32. The position estimation unit 37 estimates the position of the lesion candidate region L which is the region of interest after the cessation determination, and outputs the estimated position of the lesion candidate region L to the display determination unit 35. The estimation method of the position of the lesion candidate region L will be described later.

Figure 13:
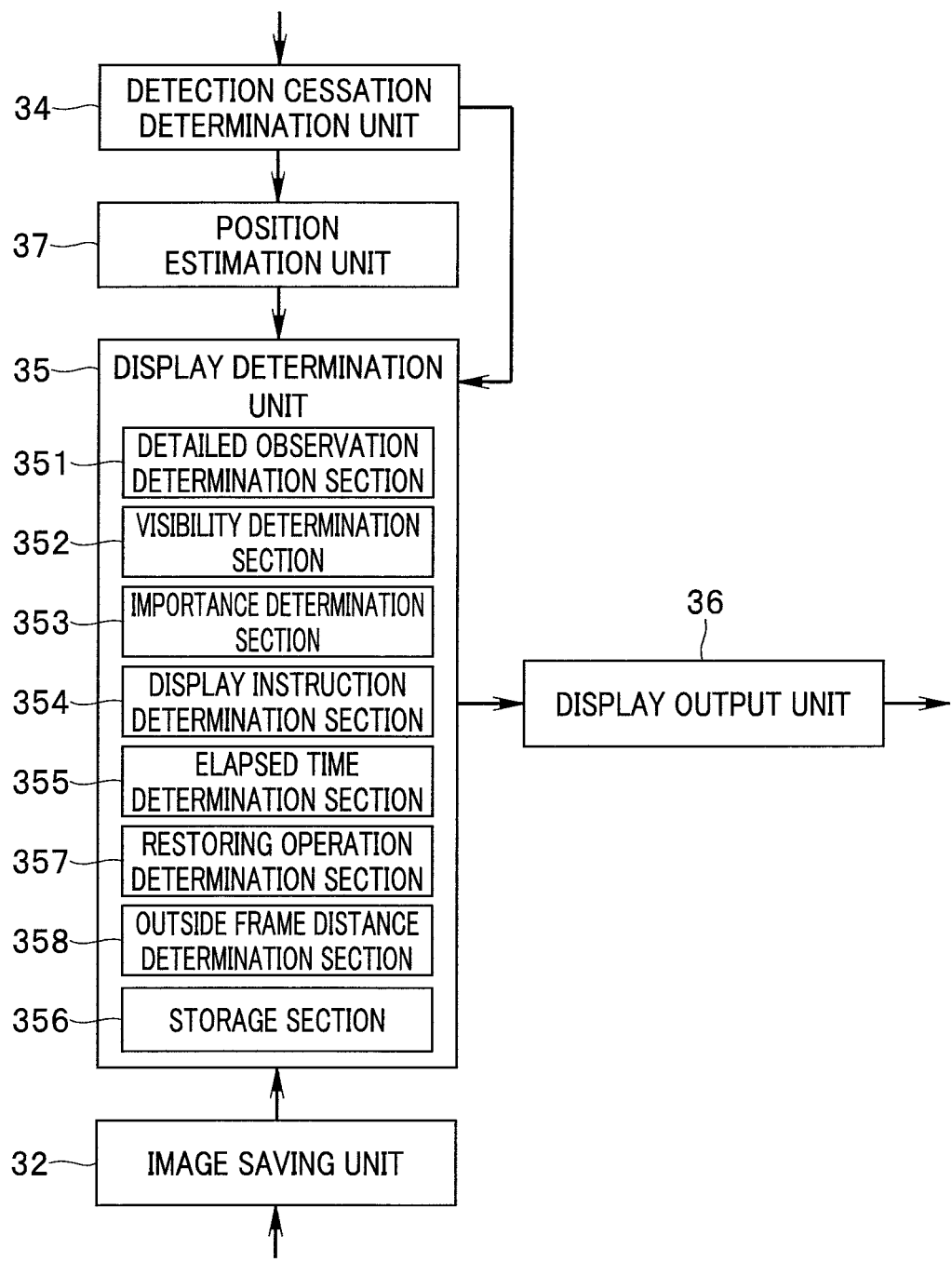
FIG. 13 is a functional block diagram illustrating a configuration of a display determination unit in the second embodiment of the present invention.

FIG. 13 is a functional block diagram illustrating a configuration of a display determination unit 35 according to the present embodiment. As described in the first embodiment, the display determination unit 35 performs the display propriety determination as the determination of whether to display the assisting information on the screen of the display unit 4. The assisting information is for assisting to cause the lesion candidate region L as the region of interest, the detection of which has ceased, to be restored on the screen of the display unit 4. In the present embodiment, the display determination unit 35 includes a restoring operation determination section 357 and an outside frame distance determination section 358, in addition to the plurality of determination sections and the storage section 356 in the first embodiment.

The restoring operation determination section 357 calculates a restoring operation parameter that changes depending on whether the restoring operation for operating the endoscope 1 to cause the lesion candidate region L as the region of interest to be restored on the screen of the display unit 4, and performs a display propriety determination based on the calculated restoring operation parameter. The restoring operation parameter is defined so as to become a larger value, as it becomes less likely that the restoring operation is performed, for example.

In the present embodiment, the restoring operation parameter is calculated based on a change in the estimated position of the lesion candidate region L, which is estimated by the position estimation unit 37. When the estimated position of the lesion candidate region L changes so as to be away from an arbitrary point on the present observation image G1, it is less likely that the restoring operation is performed. Therefore, in such a case, the restoring operation parameter is calculated to be a large value.

The outside frame distance determination section 358 calculates an outside frame distance, which is a distance from the outer edge of the observation image G1 to the estimated position of the lesion candidate region L estimated by the position estimation unit 37 and performs a display propriety determination based on the calculated outside frame distance.

In the present embodiment, the display determination unit 35 decides the contents of the determination result to be outputted to the display output unit 36, based on at least the respective determination results of the restoring operation determination section 357 and the outside frame distance determination section 358, and outputs the decided determination result to the display output unit 36. The method of deciding the contents of the determination result is the same as the method of deciding the contents of the determination result based on the respective determination results of the plurality of determination sections in the display determination unit 35 in the first embodiment.

In addition, as described in the first embodiment, when it is determined to display the assisting information on the display unit 4 in the display propriety determination, the display output unit 36 generates an image including the assisting information as an image for display G, to output the generated image to the display unit 4. In the present embodiment, when the position of the lesion candidate region L as the region of interest is estimated in the position estimation unit 37 and it is determined to display the assisting information in the display propriety determination, the assisting information processing section 362 in the display output unit 36 performs processing for changing the assisting information in accordance with the estimated position of the lesion candidate region L, as the assisting information display processing. In this case, the assisting information processing section 362 receives the estimated position of the lesion candidate region L from the position estimation unit 37. Note that the position estimation unit 37 may output the estimated position of the lesion candidate region L to the assisting information processing section 362 through the display determination unit 35, or may output the estimated position of the lesion candidate region L directly to the assisting information processing section 362.

(Estimation Method of Position of Lesion Candidate Region)

Next, description will be made on the estimation method of the position of the lesion candidate region L in the position estimation unit 37. The position estimation unit 37 generates first displacement information and second displacement information, and estimates the position of the lesion candidate region L based on the first displacement information and the second displacement information.

First, the first displacement information will be described. When the lesion candidate region L is continuously detected, that is, the detection cessation determination unit 34 determines that the detection of the lesion candidate region L does not cease, the position estimation unit 37 generates the first displacement information which is information indicating the displacement amount and displacement direction of the lesion candidate region L.

The position estimation unit 37 generates the first displacement information as described below, for example. First, the position estimation unit 37 calculates the gravity center of the lesion candidate region L based on the lesion candidate information detected from each of the observation images G1 of consecutive two frames. Next, the position estimation unit 37 calculates a first motion vector indicative of the motion of the gravity center of the lesion candidate region L between the two consecutive frames. Then, the position estimation unit 37 calculates the velocity and acceleration of the gravity center based on the first motion vector. After that, the position estimation unit 37 generates the first displacement information based on at least one of the calculated velocity or the calculated acceleration of the gravity center.

The position estimation unit 37 repeatedly generates the first displacement information during the continuous detection of the lesion candidate region L. The generated first displacement information is stored in the storage section 371.

Next, the second displacement information will be described. When the detection of the lesion candidate region L has ceased, that is, the detection cessation determination unit 34 acquires the cessation determination indicating that the detection of the lesion candidate region L has ceased, the position estimation unit 37 generates the second displacement information which is information indicating a displacement amount and a displacement direction of an arbitrary point in the observation image G1.

The position estimation unit 37 generates the second displacement information as described below, for example. First, the position estimation unit 37 reads out the present observation image G1 (hereinafter, referred to as the first observation image G1) from the image saving unit 32. Next, the position estimation unit 37 sets an arbitrary traceable point (hereinafter, referred to as the tracking point) in the first observation image G1. Then, the position estimation unit 37 reads out an observation image G1 (hereinafter, referred to as second observation image G1) of the frame next to the frame of the first observation image G1 from the image saving unit 32. After that, the position estimation unit 37 detects the position of the tracking point in the second observation image G1. The position estimation unit 37 calculates a second motion vector indicative of the motion of the tracking point between the first observation image G1 and the second observation image G1. Next, the position estimation unit 37 calculates the velocity and the acceleration of the tracking point based on the second motion vector. Then, the position estimation unit 37 generates the second displacement information based on at least one of the calculated velocity or the calculated acceleration of the tracking point.

The position estimation unit 37 repeatedly generates the second displacement information during the cessation of the detection of the lesion candidate region L. The generated second displacement information is stored in the storage section 371.

Next, the estimation method of the position of the lesion candidate region L will be described. The position estimation unit 37 estimates the position of the lesion candidate region L at a time point after the time point of the acquisition of the cessation determination, based on the first displacement information and the second displacement information. More specifically, the position estimation unit 37 detects the motion of the object included in the observation image G1 at the time point after the time point of the acquisition of the cessation determination, by using the second displacement information, and estimates the position of the lesion candidate region L at the time point after the time point of the acquisition of the cessation determination by combining the detected motion of the object with the first displacement information.

Note that the position estimation unit 37 determines whether the lesion candidate region L is located outside the outer edge of the observation image G1 or located inside the outer edge of the observation image G1, based on the first displacement information immediately before the acquisition of the cessation determination. When determining that the lesion candidate region L is located outside the outer edge of the observation image G1, the position estimation unit 37 estimates the position of the lesion candidate region L existing in a region outside the outer edge of the observation image G1, based on the second displacement information. When determining that the lesion candidate region L is located inside the outer edge of the observation image G1, the position estimation unit 37 estimates the position of the lesion candidate region L existing in the observation image G1, based on the second displacement information.

(Contents of Display Propriety Determination)

Next, description will be made on the display propriety determination that is performed in each of the restoring operation determination section 357 and the outside frame distance determination section 358. The flowchart in FIG. 5 in the first embodiment also illustrates the display propriety determination that is performed in each of the restoring operation determination section 357 and the outside frame distance determination section 358.

First, description will be made on the display propriety determination that is performed in the restoring operation determination section 357. When the cessation determination is acquired, the restoring operation determination section 357 first calculates the restoring operation parameter (step S11 in FIG. 5). Next, the restoring operation determination section 357 compares the restoring operation parameter with the predetermined threshold (step S12 in FIG. 5). When the restoring operation parameter is equal to or larger than the predetermined threshold (YES), the restoring operation determination section 357 determines not to display the assisting information (step S13 in FIG. 5). On the other hand, when the restoring operation parameter is smaller than the predetermined threshold (NO), the restoring operation determination section 357 determines to display the assisting information (step S14 in FIG. 5). The steps S12, S13, and S14 illustrated in FIG. 5 correspond to the display propriety determination that is performed in the restoring operation determination section 357.

Note that the case where the restoring operation parameter is equal to or larger than the predetermined threshold corresponds to the case where it is estimated that the restoring operation is not performed. The case where the restoring operation parameter is smaller than the predetermined threshold corresponds to the case where it is estimated that the restoring operation is performed. The display propriety determination that is performed in the restoring operation determination section 357 may be repeatedly performed after the cessation determination at predetermined time intervals, for example.

Next, description will be made on the display propriety determination that is performed in the outside frame distance determination section 358. When the cessation determination is acquired, the outside frame distance determination section 358 first calculates the outside frame distance. The outside frame distance corresponds to the parameter in the step S11 in FIG. 5. Next, the outside frame distance determination section 358 compares the outside frame distance with the predetermined threshold (step S12 in FIG. 5). When the outside frame distance is equal to or larger than the predetermined threshold (YES), the outside frame distance determination section 358 determines not to display the assisting information (step S13 in FIG. 5). On the other hand, when the outside frame distance is smaller than the predetermined threshold (NO), the outside frame distance determination section 358 determines to display the assisting information (step S14 in FIG. 5). The steps S12, S13, and S14 illustrated in FIG. 5 correspond to the display propriety determination that is performed in the outside frame distance determination section 358.

Note that the display propriety determination that is performed in the outside frame distance determination section 358 may be repeatedly performed after the cessation determination at predetermined time intervals, for example.

(Example of Assisting Information)

Figure 14:
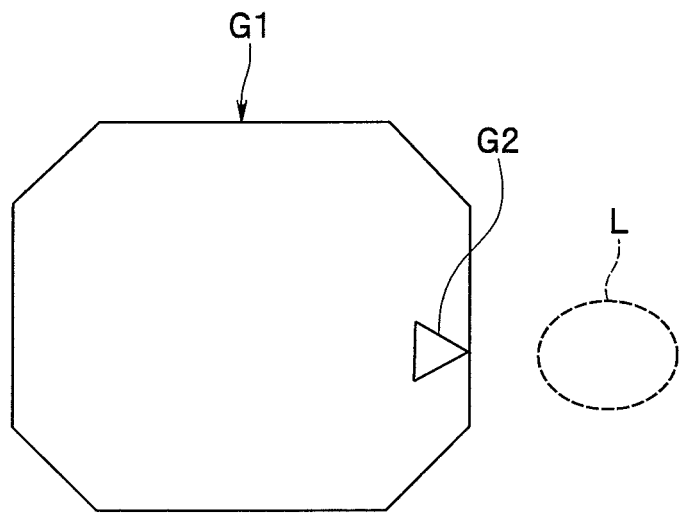
FIG. 14 is an explanatory diagram illustrating a first example of assisting information in the second embodiment of the present invention.

Next, description will be made on an example of processing for changing the assisting information in accordance with the estimated position of the lesion candidate region L. The processing is performed when the position of the lesion candidate region L as the region of interest is estimated and it is determined to display the assisting information in the display propriety determination in the position estimation unit 37. FIG. 14 is an explanatory diagram illustrating a first example of the assisting information. FIG. 14 illustrates the state where the lesion candidate region L has disappeared from the observation image G1 by moving outside the outer edge of the observation image G1, similarly in the state illustrated in FIG. 9 in the first embodiment. FIG. 14 illustrates the case where the position of the lesion candidate region L estimated by the position estimation unit 37 is farther from the outer edge of the observation image G1 than in the state illustrated in FIG. 9. As illustrated in FIGS. 9 and 14, the assisting information processing section 362 may increase the size of the alert image G2 (triangle) which is the assisting information, as the distance from the outer edge of the observation image G1 to the lesion candidate region L becomes longer.

Figure 15:
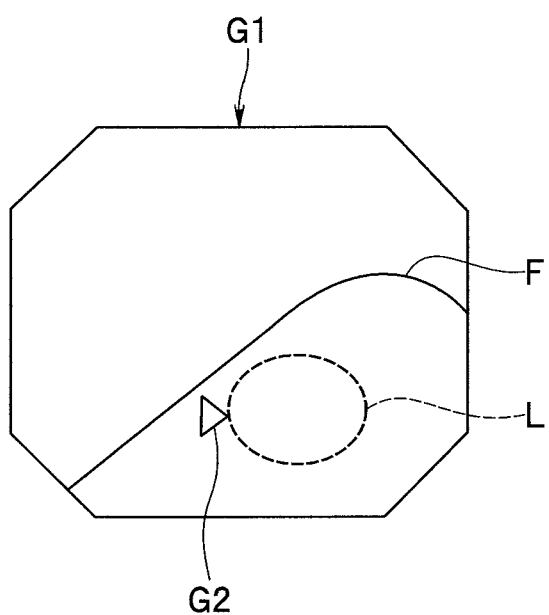
FIG. 15 is an explanatory diagram illustrating a second example of the assisting information in the second embodiment of the present invention.

FIG. 15 is an explanatory diagram illustrating a second example of the assisting information. FIG. 15 illustrates the state where the lesion candidate region L has disappeared from the observation image G1 by the lesion candidate region L being hidden in the back side of the folds F, similarly in the state illustrated in FIG. 11 in the first embodiment. FIG. 15 illustrates the example in which the position of the lesion candidate region L estimated by the position estimation unit 37 has changed from the state illustrated in FIG. 9. As illustrated in FIGS. 11 and 15, the assisting information processing section 362 may change the position of the alert image G2 (triangle) as the assisting information so as to follow the change in the estimated position of the lesion candidate region L.

(Working and Effect)

Next, a working and an effect unique to the present embodiment will be described. In the present embodiment, the position estimation unit 37 estimates the position of the lesion candidate region L as the region of interest at a time point after the time point of the acquisition of the cessation determination. The display determination unit 35 performs the display propriety determination based on at least the estimated position of the lesion candidate region L. With such a configuration, the present embodiment enables appropriate display of the assisting information. Hereinafter, the effect will be described in detail.

In the case where the lesion candidate region L as the region of interest has disappeared from the screen of the display unit 4, when the restoring operation is not performed, it is preferable not to display the assisting information in order to reduce the burden on the user of the endoscope 1 and prevent another lesion candidate region L from being hidden by the assisting information. In the present embodiment, the display determination unit 35 includes the restoring operation determination section 357. The restoring operation determination section 357 calculates the restoring operation parameter based on the change in the estimated position of the lesion candidate region L. Based on the calculated restoring operation parameter, in the case where it is estimated that the restoring operation is not performed, the restoring operation determination section 357 determines not to display the assisting information, while in the case where it is estimated that the restoring operation is performed, the restoring operation determination section 357 determines to display the assisting information. With such a configuration, the present embodiment enables appropriate display of the assisting information.

Note that the restoring operation is performed in the case where the user of the endoscope 1 has an intention to cause the disappeared lesion candidate region L to be restored and observe the restored lesion candidate region L after the cessation determination. According to the present embodiment, the restoring operation determination section 357 is capable of estimating the user's intention after the cessation determination.

Furthermore, when the lesion candidate region L has moved outside the outer edge of the observation image G1 and the distance from the outer edge of the observation image G1 to the lesion candidate region L is sufficiently long, it is more likely that the user does not have an intention to cause the disappeared lesion candidate region L to be restored and observe the restored lesion candidate region L. In the present embodiment, the display determination unit 35 includes the outside frame distance determination section 358. The outside frame distance determination section 358 determines not to display the assisting information when the outside frame distance becomes long to a certain extent. With such a configuration, the present embodiment enables appropriate display of the assisting information.

Other configurations, working, and effect of the present embodiment are the same as those of the first embodiment.

Third Embodiment

Figure 16:
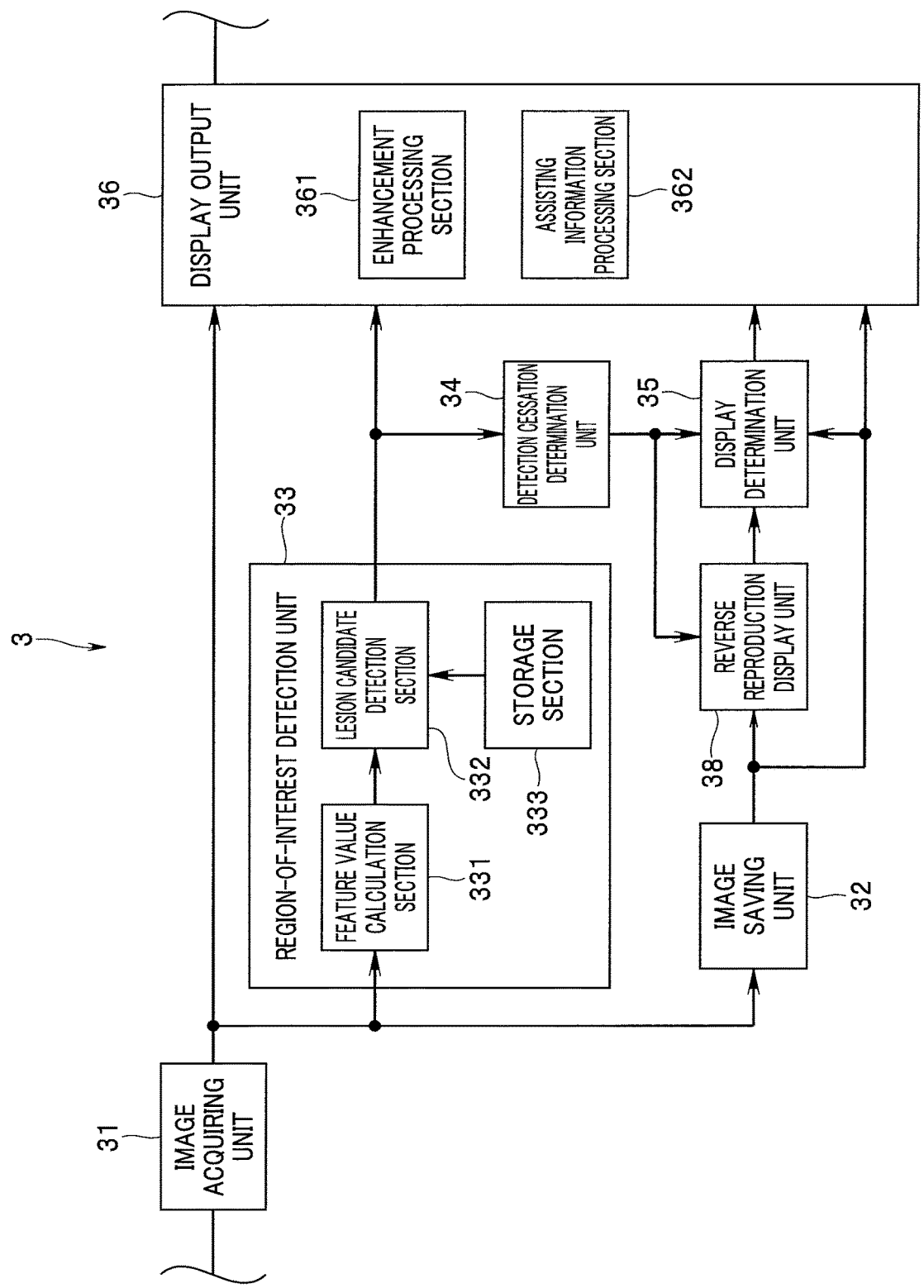
FIG. 16 is a functional block diagram illustrating a configuration of an image processing apparatus according to a third embodiment of the present invention.

Next, description will be made on an image processing apparatus according to the third embodiment of the present invention. FIG. 16 is a functional block diagram illustrating the configuration of the image processing apparatus according to the present embodiment. The image processing apparatus 3 according to the present embodiment includes a reverse reproduction display unit 38.

The reverse reproduction display unit 38 is configured to receive the determination result of the detection cessation determination unit 34. The reverse reproduction display unit 38 is configured to be capable of reading out the observation image G1 saved in the image saving unit 32. The reverse reproduction display unit 38 reads out a plurality of observation images G1 saved in the image saving unit 32 in a time-series order from a first time point of the acquisition of the cessation determination in the detection cessation determination unit 34 to a second time point after the first time point. Then, the reverse reproduction display unit 38 uses the read plurality of observation images G1 to generate a moving image G3 displayed in an order reverse to the above-described time-series order on the display unit 4 (see FIG. 1) and output the generated moving image G3 to the display output unit 36.

In addition, as described in the first embodiment, when it is determined to display the assisting information on the display unit 4 in the display propriety determination in the display determination unit 35, the display output unit 36 generates an image including the assisting information as an image for display G and output the generated image to the display unit 4. In the present embodiment, the display output unit 36 uses the moving image G3 as the assisting information, in addition to the alert image G2 described in the first embodiment.

Figure 17:
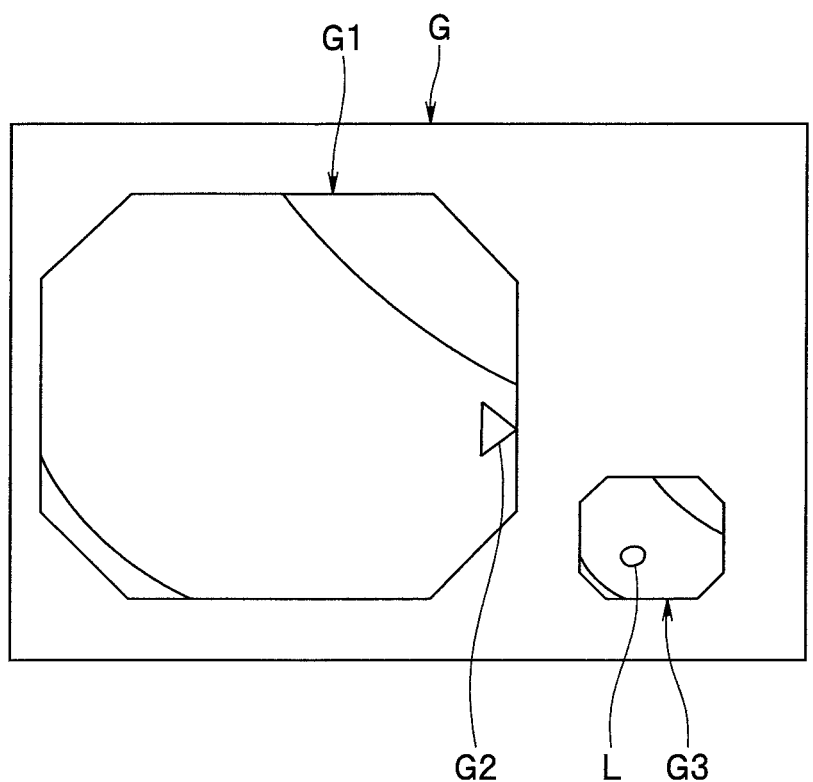
FIG. 17 is an explanatory diagram illustrating one example of an image for display in the third embodiment of the present invention.

FIG. 17 illustrates one example of the image for display G in the present embodiment. FIG. 17 illustrates the state where the lesion candidate region L as the region of interest has disappeared from the observation image G1 by moving outside the outer edge of the observation image G1, similarly in the state illustrated in FIG. 9 in the first embodiment. In the example illustrated in FIG. 17, the moving image G3 is displayed next to the observation image G1.

Note that the determination of whether to display the moving image G3 may be performed separately from the determination of whether to display the alert image G2. In this case, the display determination unit 35 determines whether to display the moving image G3 based on the instruction of whether to display the moving image G3, for example. The instruction of whether to display the moving image G3 may be acquired through the display instruction unit 6 illustrated in FIG. 1 in the first embodiment, for example.

Other configurations, working, and effect of the present embodiment are the same as those of the first embodiment.

The present invention is not limited to the above-described embodiments, and it goes without saying that various changes and modifications are possible in a range without changing the gist of the present invention. For example, the hardware configuration of the image processing apparatus 3 is not limited to the example described with reference to FIG. 2. Specifically, for example, the image acquiring unit 31, the region-of-interest detection unit 33, the detection cessation determination unit 34, the display determination unit 35, the display output unit 36, the position estimation unit 37 (second embodiment), and the reverse reproduction display unit 38 (third embodiment) of the image processing apparatus 3 may be implemented by one processor, or by a plurality of processors. In the latter case, the image acquiring unit 31, the region-of-interest detection unit 33, the detection cessation determination unit 34, the display determination unit 35, the display output unit 36, the position estimation unit 37, and the reverse reproduction display unit 38 may be implemented respectively by different processors.

What is claimed is:

1. An endoscopic image processing apparatus comprising:
a processor configured to:
acquire an image of an object photographed by an endoscope;
output an image for display including at least the acquired image to a monitor apparatus;
detect a region of interest included in the acquired image;
determine whether a detection of the region of interest has ceased;
calculate a detailed observation parameter that changes depending on whether the region of interest is observed in detail, the detailed observation parameter being calculated based on at least one of a shape change amount of the region of interest, a moving amount of the region of interest, or an observation mode of the endoscope;
perform a display propriety determination based on the detailed observation parameter, in response to acquiring a cessation determination, the cessation determination indicating a determination result that the detection of the region of interest has ceased, the display propriety determination being a determination of whether to display assisting information on the monitor apparatus, the assisting information being information for assisting to cause the region of interest, the detection of which has ceased, to be restored on a screen of the monitor apparatus;
output an image further including the assisting information to the monitor apparatus, as the image for display, in response to a determination to display the assisting information being made in the display propriety determination; and
output an image not including the assisting information to the monitor apparatus, as the image for display, in response to a determination not to display the assisting information being made in the display propriety determination.

2. The endoscopic image processing apparatus according to claim 1,
wherein the processor is configured to:
calculate a visibility parameter that changes depending on an easiness of visual recognition of the region of interest; and
perform the display propriety determination based on the visibility parameter and the detailed observation parameter.

3. The endoscopic image processing apparatus according to claim 2,
wherein the visibility parameter is calculated based on at least one of a color, a shape, or a texture of the region of interest.

4. The endoscopic image processing apparatus according to claim 1,
wherein the processor is configured to:
calculate an importance of the region of interest; and
perform the display propriety determination based on the importance of the region of interest and the detailed observation parameter.

5. The endoscopic image processing apparatus according to claim 4, wherein the importance of the region of interest is calculated based on at least one of a color, a shape, or a texture of the region of interest.

6. The endoscopic image processing apparatus according to claim 1,
wherein the processor is configured to:
measure an elapsed time from a time point of acquisition of the cessation determination; and
perform the display propriety determination based on the elapsed time from the time point of acquisition of the cessation determination and the detailed observation parameter.

7. The endoscopic image processing apparatus according to claim 1,
wherein the processor is configured to:
estimate a position of the region of interest after the cessation determination;
in response to making the determination to display the assisting information,
calculate a distance from an outer edge of the image to the position of the region of interest estimated; and
perform the display propriety determination based on the calculated distance and the detailed observation parameter.

8. The endoscopic image processing apparatus according to claim 1,
wherein the processor is configured to:
calculate a restoring operation parameter that changes depending on whether a restoring operation for operating the endoscope so as to cause the region of interest to be restored on the screen of the monitor apparatus is performed; and
perform the display propriety determination based on the restoring operation parameter and the detailed observation parameter.

9. The endoscopic image processing apparatus according to claim 8,
wherein the processor is further configured to:
estimate a change in a position of the region of interest after the cessation determination; and in response to making the determination to display the assisting information, and calculate the restoring operation parameter based on the change in the position of the region of interest.

10. The endoscopic image processing apparatus according to claim 1,
wherein the processor is configured to:
save images acquired in a time-series order from a first time point of acquisition of the cessation determination to a second time point after the first time point; and
generate, based on the saved images acquired in time-series order, a moving image to be displayed in an order reverse to the time-series order on the monitor apparatus as the assisting information.

11. An endoscopic image processing method comprising:
acquiring an image of an object photographed by an endoscope;
outputting an image for display including at least the acquired image to a monitor apparatus;
detecting a region of interest included in the acquired image;
determining a detection of the region of interest has ceased;
calculating a detailed observation parameter that changes depending on whether the region of interest is observed in detail, the detailed observation parameter being calculated based on at least one of a shape change amount of the region of interest, a moving amount of the region of interest, or an observation mode of the endoscope;
performing a display propriety determination based on the detailed observation parameter, in response to acquiring a cessation determination, the cessation determination indicating a determination result that the detection of the region of interest has ceased, the display propriety determination being a determination of whether to display assisting information on the monitor apparatus, the assisting information being information for assisting to cause the region of interest, the detection of which has ceased, to be restored on a screen of the monitor apparatus;
outputting an image further including the assisting information to the monitor apparatus, as the image for display, in response to a determination to display the assisting information being made in the display propriety determination; and
outputting an image not including the assisting information is outputted to the monitor apparatus, as the image for display, in response to a determination not to display the assisting information being made in the display propriety determination.

12. The endoscopic image processing method according to claim 11, comprising:
calculating a visibility parameter that changes depending on an easiness of visual recognition of the region of interest; and
performing the display propriety determination based on the visibility parameter and the detailed observation parameter.

13. The endoscopic image processing method according to claim 11, comprising:
calculating an importance of the region of interest; and
performing the display propriety determination based on the importance of the region of interest and the detailed observation parameter.

14. The endoscopic image processing method according to claim 11, comprising:
measuring an elapsed time from a time point of acquisition of the cessation determination; and
performing the display propriety determination based on the elapsed time from the time point of acquisition of the cessation determination and the detailed observation parameter.

15. The endoscopic image processing method according to claim 11, comprising:
estimating a position of the region of interest after the cessation determination; and in response to making the determination to display the assisting information
calculating a distance from an outer edge of the image to the position of the region of interest estimated; and
performing the display propriety determination based on the calculated distance and the detailed observation parameter.

16. The endoscopic image processing method according to claim 11, comprising:
calculating a restoring operation parameter that changes depending on whether a restoring operation for operating the endoscope so as to cause the region of interest to be restored on the screen of the monitor apparatus is performed and
performing the display propriety determination based on the restoring operation parameter and the detailed observation parameter.

17. The endoscopic image processing method according to claim 11, comprising:
- saving images acquired in a time-series order from a first time point of acquisition of the cessation determination to a second time point after the first time point; and
- generating, based on the saved images acquired in time-series order, a moving image to be displayed in an order reverse to the time-series order on the monitor apparatus as the assisting information.

18. A non-transitory computer readable recording medium on which a program is recorded, the program causing a computer to at least execute:
- acquiring an image of an object photographed by an endoscope;
- outputting an image for display including at least the acquired image to a monitor apparatus;
- detecting a region of interest included in the acquired image;
- determining whether a detection of the region of interest has ceased;
- calculating a detailed observation parameter that changes depending on whether the region of interest is observed in detail, the detailed observation parameter being calculated based on at least one of a shape change amount of the region of interest, a moving amount of the region of interest, or an observation mode of the endoscope;
- performing a display propriety determination based on the detailed observation parameter, in response to acquiring a cessation determination is acquired, the cessation determination indicating a determination result that the detection of the region of interest has ceased, the display propriety determination being a determination of whether to display assisting information on the monitor apparatus, the assisting information being information for assisting to cause the region of interest, the detection of which has ceased, to be restored on a screen of the monitor apparatus;
- outputting an image further including the assisting information to the monitor apparatus, as the image for display, in response to a determination to display the assisting information being made in the display propriety determination; and
- outputting an image not including the assisting information to the monitor apparatus, as the image for display, in response to a determination not to display the assisting information being made in the display propriety determination.

* * * * *